(12) United States Patent
Maurer et al.

(10) Patent No.: US 7,575,857 B2
(45) Date of Patent: Aug. 18, 2009

(54) SCREENING METHOD FOR IDENTIFYING PROTECTIVE SUBSTANCES FOR TREATING NEURODEGENERATIVE AND/OR ISCHEMIC DISORDERS

(75) Inventors: Martin Maurer, Heidelberg (DE); Wolfgang Kuschinsky, Heidelberg (DE); Armin Schneider, Heidelberg (DE); Alfred Bach, Edingen-Neckarhausen (DE)

(73) Assignee: SYGNIS Bioscience GmbH & Co. KG, Heidelberg (DE)

( * ) Notice: Subject to any disclaimer, the term of this patent is extended or adjusted under 35 U.S.C. 154(b) by 43 days.

(21) Appl. No.: 10/507,710

(22) PCT Filed: Mar. 14, 2003

(86) PCT No.: PCT/EP03/02718

§ 371 (c)(1),
(2), (4) Date: Jun. 16, 2005

(87) PCT Pub. No.: WO03/076950

PCT Pub. Date: Sep. 18, 2003

(65) Prior Publication Data

US 2005/0239069 A1    Oct. 27, 2005

(30) Foreign Application Priority Data

Mar. 14, 2002    (DE)    ............... 102 11 369

(51) Int. Cl.
*C12Q 1/00*    (2006.01)
(52) U.S. Cl. ......................................... 435/4
(58) Field of Classification Search ............... None
See application file for complete search history.

(56) References Cited

U.S. PATENT DOCUMENTS 6,153,427 A    11/2000    King et al.

OTHER PUBLICATIONS

Burmester et al., a vertebrate globin expressed in the brain, Nature, Sep. 28, 2000, vol. 407, No. 6803, pp. 520-523.*
Kanamori et al., induction of erythroid gene-expression by microcell fusion, experimental cell research, 1997 vol. 232, pp. 90-96.*
Frietsch et al, Hemoglobin Is Expressed by Neurons in the Brain of Transgenic Mice Overexpressing Erythropoietin (EPO), Anesthesiology 2002 vol. 96: A761, p. 1.*
Blau et al. Blood, 1993, 81(2):529-37.*
Kaiho et al. Analytical Biochemistry, vol. 149, Issue 1, Aug. 15, 1985, pp. 117-120—Abstract only.*
Pace et al., "Transgenic mouse model of pharmacologic induction of fetal hemoglobin: studies using a new ribonucleotide reductase inhibitor, Didox," *Am. J. Hematol.*, 452(2):136-141 (1994) abstract only.
Wagner et al., "Chronic inborn erythrocytosis leads to cardiac dysfunction and premature death in mice overexpressing erythropoietin,"*Blood*, 97(2):536-542 (2001).
Broyles et al., "Specific repression of beta-globin promoter activity by nuclear ferritin", PNAS, 98(16):9145-9150 (2001).
Brines et al., "Erythropoietin crosses the blood-brain barrier to protect against experimental brain injury" PNAS, 97(19):10526-10531 (2000).
Dover et al., "Hydroxyurea Induction of Hemoglobin F Production in Sickle Cell Disease: relationship Between Cytotoxicity and F Cell Production", Blood, 67(3):735-738 (1986).
International Search Report.
Maurer et al., "Analysis of brain mRNA of EPO overexpressing mice", Pfluegers Archiv. European Journal of Physiology, 441:6S:R174 (2001).
D'Arcangelo, Gabriella et al., "Activation of Codependent Transcription Factors Is Required for Transcriptional Induction of the *vgf* Gene by Nerve Growth Factor and Ras", Molecular and Cellular Biology, Sep. 1996, pp. 4621-4631, vol. 16, No. 9, American Society for Microbiology, Washington, D.C.
Ruschitzka, Frank T. et al., "Nitric oxide prevents cardiovascular disease and determines survival in polyglobulic mice overexpressing erythropoietin", Proceedings of the National Academy of Sciences of USA, Oct. 10, 2000, pp. 11609-11613, vol. 97, No. 21, National Academy of Sciences, Washington, D.C.

* cited by examiner

*Primary Examiner*—Suzanne M. Noakes
(74) *Attorney, Agent, or Firm*—Townsend and Townsend and Crew LLP

(57) ABSTRACT

The present invention relates to a screening method for the identification of protective substances which influence haemoglobin formation in neuronal, myocardial and/or skeleto-muscular cells, as well as to recombinant constructs, host cells and transgenic animals for the implementation of this method. In addition, the present invention relates to a diagnostic method for the differential diagnosis of neurodegenerative and/or ischaemic diseases in mammals and the use of haemoglobin, a globin or a mutein or fusion protein thereof or a corresponding nucleic acid for the treatment of neurodegenerative and/or ischaemic diseases in mammals. The invention furthermore relates to constructs for gene therapy of such diseases.

10 Claims, 23 Drawing Sheets

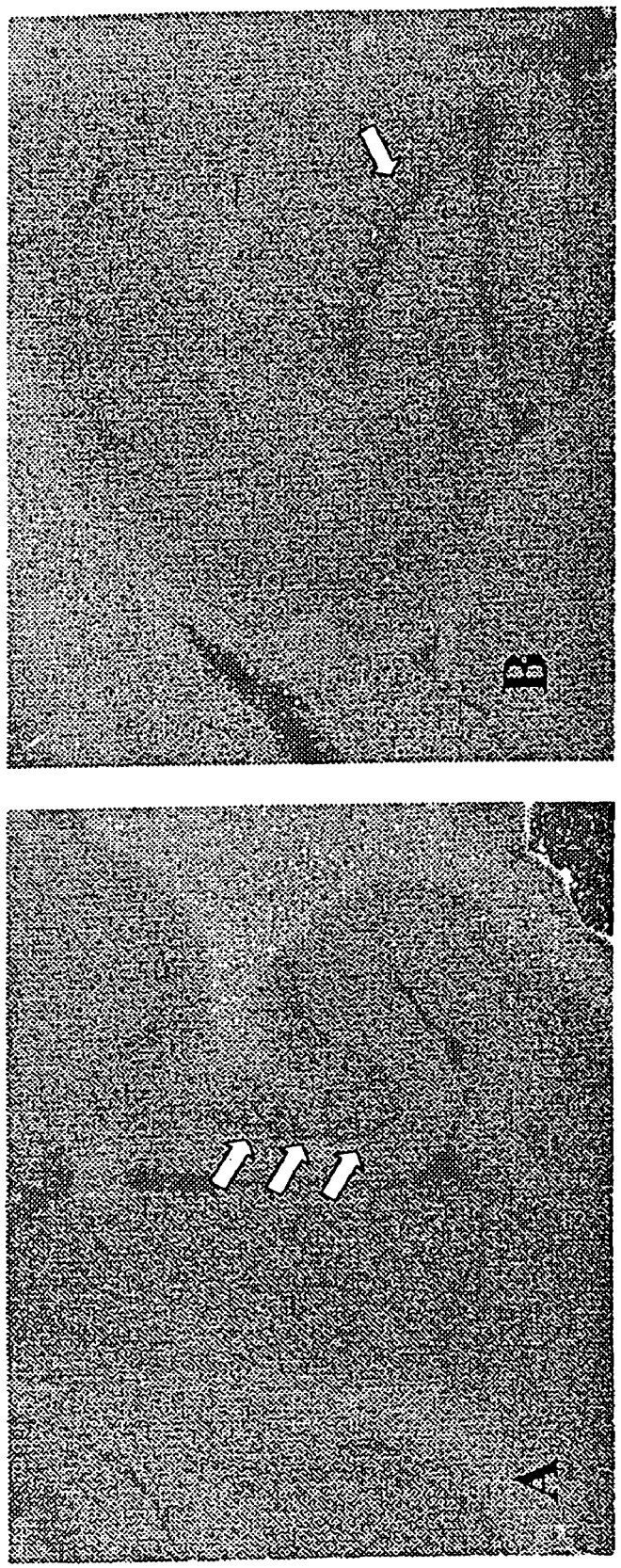
FIG. 7.1

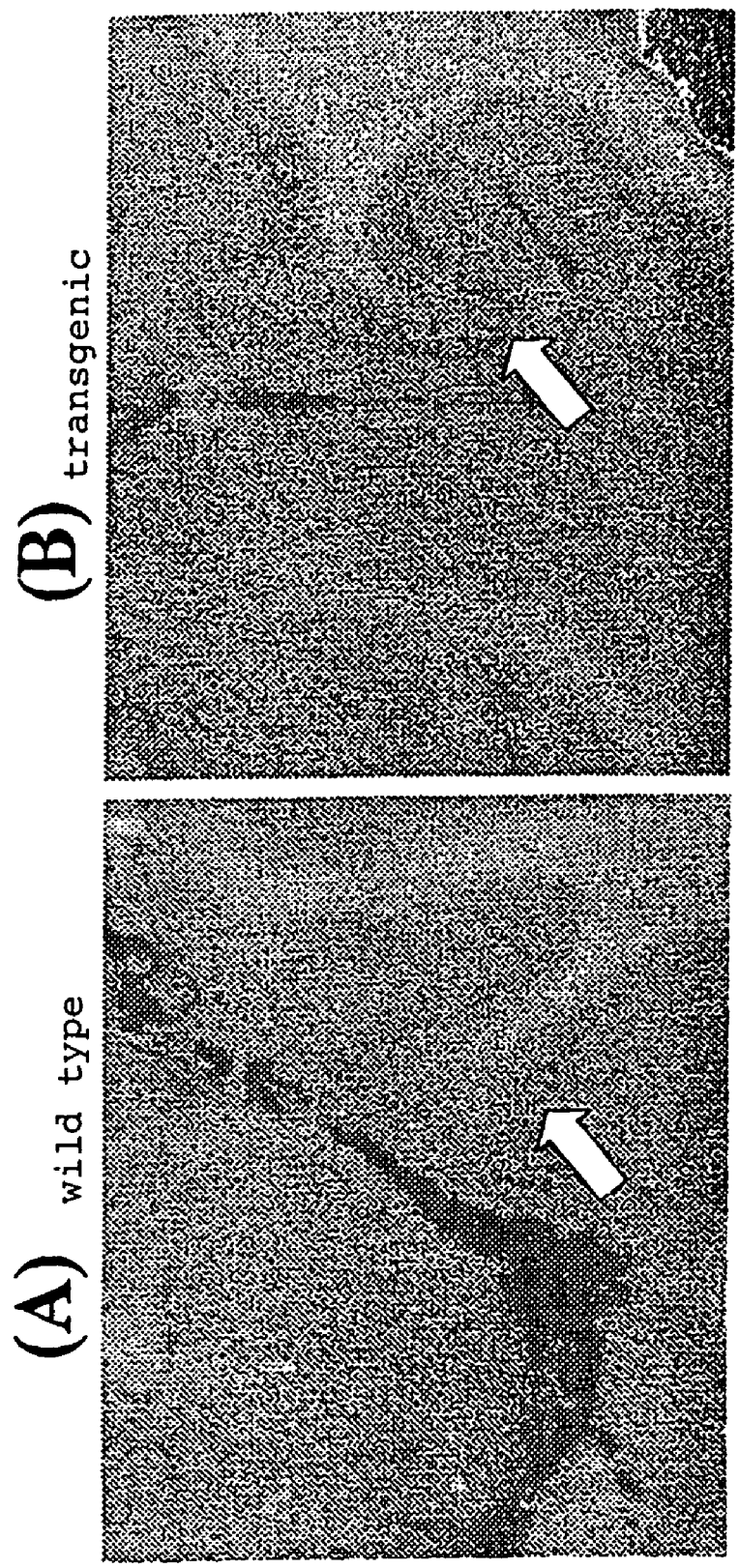
FIG. 8.1

```
                        SEQUENCE LISTING

<160> NUMBER OF SEQ ID NOS: 17

<210> SEQ ID NO 1
<211> LENGTH: 20
<212> TYPE: DNA
<213> ORGANISM: Artificial Sequence
<220> FEATURE:
<223> OTHER INFORMATION: synthetic cyclophilin forward primer

<400> SEQUENCE: 1
accccaccgt gttcttcgac                                               20

<210> SEQ ID NO 2
<211> LENGTH: 20
<212> TYPE: DNA
<213> ORGANISM: Artificial Sequence
<220> FEATURE:
<223> OTHER INFORMATION: synthetic cyclophilin reverse primer

<400> SEQUENCE: 2
catttgccat ggacaagatg                                               20

<210> SEQ ID NO 3
<211> LENGTH: 18
<212> TYPE: DNA
<213> ORGANISM: Artificial Sequence
<220> FEATURE:
<223> OTHER INFORMATION: synthetic haemoglobin alpha forward primer

<400> SEQUENCE: 3
ggtgccctgt ctgctctg                                                 18

<210> SEQ ID NO 4
<211> LENGTH: 20
<212> TYPE: DNA
<213> ORGANISM: Artificial Sequence
<220> FEATURE:
<223> OTHER INFORMATION: synthetic haemoglobin alpha reverse primer

<400> SEQUENCE: 4
ggcagcttaa cggtacttgg                                               20

<210> SEQ ID NO 5
<211> LENGTH: 26
<212> TYPE: DNA
<213> ORGANISM: Artificial Sequence
<220> FEATURE:
<223> OTHER INFORMATION: synthetic hybridisation probe for haemoglobin

<400> SEQUENCE: 5
cttacatcaa agtgagggaa gtaggt                                        26

<210> SEQ ID NO 6
<211> LENGTH: 22
<212> TYPE: DNA
<213> ORGANISM: Artificial Sequence
<220> FEATURE:
<223> OTHER INFORMATION: synthetic primer rm_a_glob_s

<400> SEQUENCE: 6
gggaagattg gtggccatgg tg                                            22
```

<210> SEQ ID NO 7
<211> LENGTH: 24
<212> TYPE: DNA
<213> ORGANISM: Artificial Sequence
<220> FEATURE:
<223> OTHER INFORMATION: synthetic primer rm_a_glob_a

<400> SEQUENCE: 7
ggcaaggaat ttgtccagag aggc                                          24

<210> SEQ ID NO 8
<211> LENGTH: 24
<212> TYPE: DNA
<213> ORGANISM: Artificial Sequence
<220> FEATURE:
<223> OTHER INFORMATION: synthetic primer rm_b_glob_s

<400> SEQUENCE: 8
ctgactgatg ctgagaaggc tgct                                          24

<210> SEQ ID NO 9
<211> LENGTH: 22
<212> TYPE: DNA
<213> ORGANISM: Artificial Sequence
<220> FEATURE:
<223> OTHER INFORMATION: synthetic primer rm_b_glob_a

<400> SEQUENCE: 9
tccagccacc accttctgga ag                                            22

<210> SEQ ID NO 10
<211> LENGTH: 21
<212> TYPE: DNA
<213> ORGANISM: Artificial Sequence
<220> FEATURE:
<223> OTHER INFORMATION: synthetic primer alas_m_LC_1s

<400> SEQUENCE: 10
acagacctgc tgagcaccat g                                             21

<210> SEQ ID NO 11
<211> LENGTH: 21
<212> TYPE: DNA
<213> ORGANISM: Artificial Sequence
<220> FEATURE:
<223> OTHER INFORMATION: synthetic primer alas_m_LC_1as

<400> SEQUENCE: 11
agccagctcc tgttcaagct c                                             21

<210> SEQ ID NO 12
<211> LENGTH: 21
<212> TYPE: DNA
<213> ORGANISM: Artificial Sequence

```
<220> FEATURE:
<223> OTHER INFORMATION: synthetic primer daldh_m_1s

<400> SEQUENCE: 12
ccaactattg aggctgtccg t                                                21

<210> SEQ ID NO 13
<211> LENGTH: 21
<212> TYPE: DNA
<213> ORGANISM: Artificial Sequence
<220> FEATURE:
<223> OTHER INFORMATION: synthetic primer daldh_m_1as

<400> SEQUENCE: 13
catgagcatg tcagctcctt c                                                21

<210> SEQ ID NO 14
<211> LENGTH: 21
<212> TYPE: DNA
<213> ORGANISM: Artificial Sequence
<220> FEATURE:
<223> OTHER INFORMATION: synthetic primer ngl_m_LC_1s

<400> SEQUENCE: 14
gagtcagagc tgatccggca g                                                21

<210> SEQ ID NO 15
<211> LENGTH: 21
<212> TYPE: DNA
<213> ORGANISM: Artificial Sequence
<220> FEATURE:
<223> OTHER INFORMATION: synthetic primer ngl_m_LC_1as

<400> SEQUENCE: 15
caggcacttc tccagcatgt a                                                21

<210> SEQ ID NO 16
<211> LENGTH: 64
<212> TYPE: DNA
<213> ORGANISM: Artificial Sequence
<220> FEATURE:
<223> OTHER INFORMATION: synthetic oligo aGlo 1-s

<400> SEQUENCE: 16
gatccccttc cttgcctctg tgagcattca agagatgctc acagaggcaa ggaattttttg      60 gaaa                                                                   64

<210> SEQ ID NO 17
<211> LENGTH: 63
<212> TYPE: DNA
<213> ORGANISM: Artificial Sequence
<220> FEATURE:
<223> OTHER INFORMATION: synthetic oligo aGlo1-as

<400> SEQUENCE: 17
gcttttccaa aaattccttg cctctgtgag catctcttga atgctcacag aggcaaggaa       60
ggg                                                                    63
```

SCREENING METHOD FOR IDENTIFYING PROTECTIVE SUBSTANCES FOR TREATING NEURODEGENERATIVE AND/OR ISCHEMIC DISORDERS

The present invention relates to a screening method for the identification of protective substances which influence the formation of haemoglobin in neuronal, myocardial and/or skeletomuscular cells as well as to recombinant constructs, host cells and transgenic animals for the implementation of this method. In addition, the present invention relates to a diagnostic method for the differential diagnosis of neurodegenerative and/or ischaemic diseases in maminals and the use of haemoglobin, a globin or a mutein or fusion protein thereof or a corresponding nucleic acid for the treatment of neurodegenerative and/or ischaemic diseases in maminals. The invention furthermore relates to constructs for gene therapy of such diseases.

According to the statistics issued by the Federal Statistics Office, cerebrovascular diseases cause around 90,000 deaths in the Federal Republic of Germany every year. The figures for the beginning of the 1980s show that around half of all stroke patients do not survive the first three weeks. Although the number of new cases is currently falling, strokes are still, alongside cardiac infarction, one of the most significant diseases in the middle age ranges.

A stroke is a severe functional disturbance of the brain which occurs abruptly after fleeting precursors and which is caused by a reduction or complete interruption in the blood supply of the circumscribed parts of the brain, associated with loss of consciousness, paralysis and speech and feeling disorders. Thanks to good medical care, people suffering from strokes survive for longer than previously, but around 50-60% of these have to live with a disability caused by neurological damage.

Erythropoietin (EPO) is an acid glycoprotein which was originally found as a haematopoetic factor in the serum of bled rabbits. It causes the induction of erythropoesis in order to combat tissue hypoxia. In this function, it has long been used in the treatment of anaemia, e.g. in dialysis patients. Apart from this erythropoetic effect, attention has been drawn recently to the effects of EPO in the central nervous system. A functional effect of EPO on the brain, especially a neuroprotective effect, was clearly proved recently (Brines et al., 2000, Proc. Natl. Acad. Sci. USA 97, 10526-31; Digicaylioglu and Lipton, 2001, Nature 412, 641-7). This includes protective effects in models of neurological diseases such as cerebral ischaemia, experimentally induced encephalomyelitis or subarachnoidal bleeding. The significance of erythropoietin for the survival of neurones in hypoxy-ischaemic conditions has been proved in many studies in vivo (Bernaudin et al., 1999, J. Cereb. Blood Flow Metab. 19, 643-651; Brines et al., 2000, loc. cit.) and in vitro (Siren et al., 2001, Proc. Natl. Acad. Sci. USA 98, 4044-4049; Digicaylioglu and Lipton, 2001, Nature 412, 641-647).

Because of its erythropoetic effect, the administration of EPO causes, however, an increase in the haematocrit alongside the neuroprotective effect, which to some extent counteracts the neuroprotective effect, since the increase in the haematocrit causes a deterioration in the rheological properties of the blood, which has a negative effect on microcirculation. There is therefore a need for substances with the protective effect of EPO but without its undesired side-effects.

One of the objects of the present invention therefore is to provide a screening method which allows the identification of new substances with a protective effect on neuronal, myocardial and/or skeletomuscular cells.

This object is solved by a screening method for the identification of protective substances which influence the formation of haemoglobin in neuronal, myocardial and/or skeletomuscular cells, comprising bringing the substance to be tested into contact with a test cell selected from neuronal, myocardial and/or skeletomuscular cells, and the demonstration of a change in haemoglobin formation in the test cell.

The screening method according to the invention is based on a protective principle hitherto unknown in maminals which is associated with a differential regulation of alpha and beta globin in the central nervous system. Surprisingly, it was found that in the brain of transgenic mice which overexpress human erythropoietin (lines tg6 and tg21; Ruschitzka et al., 2000, Proc. Natl. Acad. Sci. USA 97, 11609-13) there is an increased expression of haemoglobin both on the messenger RNA level and on the protein level. The results described in the examples show that, in the brain of the transgenic animals, messenger RNA for haemoglobin is induced roughly by a factor of 3-4 and haemoglobin protein by a factor of 2-3. There has been no description to date of any regulation and induction of haemoglobin in brain cells on the RNA or the protein level.

The term "protective substances" describes substances which have a protective effect on cells and/or on individual organs as a whole (e.g. brain or heart) in vitro (in cell culture systems) and/or in vivo (in animal models of ischaemic, hypoxic and/or neurodegenerative diseases such as stroke models, models of amyotrophic lateral sclerosis or models of Parkinson's disease) and/or in people. The application of the substance can take place before or after the harmful event.

A test for protective effect can be, for example, an in-vitro test with cultivated test cells which are exposed to harmful noxa, e.g. a hypoxic treatment, treatment with $H_2O_2$, glutamate, MPP or other harmful substances. A normal in-vitro test for protective substances is the viability investigation of cells in which the survival of or damage to the cell is examined, as described in Lindl, 2000, Zell- und Gewebekultur (Cellular and Tissue Culture), Spektrum Akad. Vlg., Heidelberg, and Sinor and Greenberg, 2000, Neurosci. Lett. 290, 213-215; other tests include studies on expression-apoptotic markers (Siren et al., 2001, Proc. Natl. Acad. Sci. USA 98, 4044-4049) or define a reduction in the infarction volume as a measure of neuroprotective effect (Brines et al., 2000, loc. cit.).

The test can also be carried out in vivo, e.g. in mice which are treated with the substance to be tested and then exposed to damage, e.g. in a stroke or cardiac infarction model. In a stroke model, the protective effect can be determined, for example, by a reduction in the infarction volume. The same also applies for the cardiac infarction model (see Brines et al., 2000, loc. cit.).

The term "neuronal (test) cell" is used for cells which are of neuronal origin or which show neurone-like growth and differentiation behaviour, i.e. which possess essential characteristics of naturally occurring nerve cells or which are derived from cells which have a neuronal identity, such as PC12 cells or neuroblastoma cells.

The term "myocardial (test) cell" is used for cells which are of myocardial origin or which show cardiomyocyte-like growth and differentiation behaviour, i.e. which possess essential characteristics of naturally occurring cardiomyocytes or which are derived from cells which have a cardiomyocytal identity, such as H9c2(2-1) cells.

The term "skeletomuscular (test) cell" is used for cells which are of skeletomuscular origin or which show skeletomuscular-like growth and differentiation behaviour, i.e. which possess essential characteristics of naturally occurring skeletomuscular cells or which are derived from cells which have a skeletomuscular identity, such as SC-71 or L6 cells.

The term "changed haemoglobin formation" describes an increase or reduction in the quantity of haemoglobin at globin RNA and haemoglobin protein level in the test cell, whereby the difference in relation to untreated control cells must have a level of significance of 5%.

The regulation of haemoglobin in neuronal, myocardial and/or skeletomuscular cells which is associated with the protective effect can be exploited for therapeutic purposes in order to find substances which provide, via a high or low regulation of the haemoglobin, a protection of neuronal, myocardial and/or skeletomuscular cells under harmful influences, e.g. ischaemia. The basic structure of such a screening system for the identification of protective substances which produce a changed haemoglobin formation in neuronal, myocardial and/or skeletomuscular cells consists of 1) cells which react to stimuli with haemoglobin induction; 2) an adding unit for various substances to be tested from a substance bank; and 3) a detection method for globin RNA or haemoglobin protein.

The screening systems according to the invention allow chemical libraries to be searched through for substances which have inhibiting or activating effects on haemoglobin formation. The identification of such substances represents the first step on the way towards the identification of new medications which specifically affect haemoglobin-associated protection.

Detection of haemoglobin is conceivable in various ways. In principle, detection can be carried out at RNA or protein level. In one embodiment of the invention, detection of the changed haemoglobin formation takes place through the detection of at least one globin RNA, preferably alpha globin and/or beta globin RNA. Under the terms of the invention, the term "globin" is used for a protein in the globin family which comprises amongst others alpha globin, beta globin and the foetal haemoglobin subunits epsilon, zeta, eta and delta (Grosveld et al., 1993, Baillieres Clin. Haematol. 6, 31-55). An overview of the members of the globin family is given by Bumester et al. in Nature 407, 520-23 (2000).

RNA can be detected in principle via a reverse transcription/polymerase chain reaction, e.g. using a PCR cycler with the possibility of quantification using SYBR Green. This can be done on a 96 or 384 well scale, after addition of the substance to be tested to neuronal, myocardial or skeletomuscular cells such as, for example, PC12 cells, derived neuroblastoma cells or primary neurones. The relative quantification of the globin RNA is possible in comparison with standard genes such as cyclophilin or S26. Similarly, detection is also possible using hybridisation methods with a suitable probe, e.g. using dot blot hybridisation.

Protein detection is possible, for example, using specialised protein microchips which can detect very small quantities of haemoglobin protein (e.g. microchips made by Zyomyx, Hayward, Calif., USA), sometimes with the use of microcapillary electrophoresis. For the protein detection, special detection properties of the haemoglobin can also be utilised, such as stainability using 2,7 diaminofluorene (DAF) or using the rapid cyanhaemiglobin method. The detection of haemoglobin could also be carried out at high flow rates in primary cell lysates using photometric methods.

An alternative to the direct detection of a changed haemoglobin formation in neuronal, myocardial and/or skeletomuscular cells can also be the use of a construct which contains, along with a reporter gene, essential components of the globin regulation to stimuli. In an alternative embodiment, the screening method according to the invention comprises the step of bringing the substance to be tested into contact with a test cell, selected from a neuronal, myocardial and skeletomuscular cell, which contains a reporter gene under the functional control of regulatory elements of at least one globin gene, and the step of detecting the reporter gene product in the test cell.

The regulatory elements can be promoter segments and enhancer elements which may lie in the 5' or 3' range of a globin gene or in its introns. These regulation elements are linked with at least one reporter gene which allows measurement of a changed protein formation. Preferably, this involves simple measurement methods (colorimetric, luminometric, fluorescence-based or radio-active) which allow the rapid measurement of a large number of test substances (see, for example, Böhm, Klebe, Kubinyi, 1996, *Wirkstoffdesign* (Substance Design), Spektrum-Verlag, Heidelberg). Suitable reporter genes are, for example, luciferase, alkaline phosphatase (preferably as secreted alkaline phosphatase), beta-galactosidase, EGFP or similar reporter genes with which the specialist is familiar. These constructs are preferably expressed in cells which possess neurone-like, cardiomyocyte-like or skeletomuscle-like properties, e.g. neuroblastoma cells or PC12 cells.

The object of the invention is, in addition, a recombinant construct which includes a reporter gene under the functional control of regulatory elements of at least one globin gene, plus a host cell and a transgenic non-human animal which contains the recombinant construct according to the invention. A substance which, in contact with a neuronal, myocardial and/or skeletomuscular cell, influences i.e. raises or lowers the haemoglobin formation and which is identifiable with the method according to the invention is also comprised by the invention. Erythropoietin is not comprised by the invention.

The realisation forming the basis for the present invention that the extent of the haemoglobin formation in neurones is related to a protective effect can be used for the diagnosis and/or treatment of human diseases, especially neurological diseases or myocardic ischaemia. A further object of the invention is therefore a method of diagnosis for the differential diagnosis of neurodegenerative and/or ischaemic diseases, comprising the step of detecting a changed haemoglobin formation in a biological sample which contains neuronal, myocardial and/or skeletomuscular cells, for example in liquor.

In one embodiment of the diagnostic method, the detection of a changed haemoglobin formation in a biological sample comprises the following steps: a) incubation of a biological sample with a known quantity of oligonucleotides which are suitable as primers for an amplification of at least one globin RNA, b) detection of the globin RNA through specific hybridisation or PCR amplification, c) comparison of the quantity of hybridising globin RNA or of nucleic acid obtained through PCR amplification with a quantity standard. The detection can also be carried out on the basis of the quantity of the haemoglobin protein. A method of diagnosis of this type comprises for example the following steps: a) incubation of a biological sample with an antibody which is specifically targeted against globin, b) detection of the antibody/antigen complex, c) comparison of these quantities of the antibody/antigen complex with a quantity standard. Similarly, it is possible to determine haemoglobin using established biochemical detection methods. A biological sample from a healthy organism is generally taken as the standard.

The method of diagnosis makes use of the property of the globin gene to regulate, e.g. to increase, the mRNA quantity of globin after particular pathophysiological stimuli, such as cerebral ischaemia. This can be used, for example, in the progression assessment of illnesses (e.g. stroke), in the assessment of therapeutic successes or in the graduation of an illness.

The method of diagnosis according to the invention is suitable for the differential diagnosis of neurological diseases and/or diseases in which chronic or acute ischaemic and/or hypoxic states can occur or are involved, especially strokes, global hypoxia after cardiac infarction or intraoperative oxygen deficiencies in the brain. Further diseases which can be diagnosed with the method of diagnosis according to the invention are neurological diseases such as multiple sclerosis, Parkinson's disease, amyotrophic lateral sclerosis, heredodegenerative ataxias, Huntington's disease, neuropathia or epilepsy, diseases in which chronic or acute ischaemia and/or hypoxia can occur or are involved, such as myocardial infarction, cardiac insufficiency, cardiomyopathies, myocarditis, pericarditis, perimyocarditis, coronary heart disease, congenital vitia with right-left shunt, Fallot's tetralogy/pentalogy, Eisenmenger syndrome, shock, ischaemia of the extremities, arterial occlusive disease (AOD), peripheral AOD (pAOD), carotid stenosis, renal artery stenosis, disorders of the microcirculation in the brain (small vessel disease), intracerebral bleeding, venous thrombosis of the brain and intracranial sinus thrombosis, angiodysplasia, subarachnoidal bleeding, vascular dementia, Biswanger's disease, subcortical arteriosclerotic encephalopathy, multiple cortical infarctions with embolisms, vasculitis, diabetic retinopathy, consequences of anaemia with different causes (e.g. aplastic anaemia, myelodysplastic syndrome, polycythaemia vera, megaloblastic anaemia, iron deficiency anaemia, renal anaemia, sphaerocytosis, haemolytic anaemia, thalassaemia, haemoglobinopathies, glucose-6-phosphate dehydrogenase deficiency, transfusion incidents, Rhesus incompatibilities, malaria, valvuloplasty, acute posthaemorrhagic anaemia, hypersplenia syndrome, lung fibroses, emphysema, lung oedema: ARDS, IRDS or relapsing lung embolisms.

A further object of the invention is to provide means of treating neurodegenerative and/or ischaemic diseases. This object is solved by the use of haemoglobin, a globin or a mutein or fusion protein thereof. The term "fusion protein" in the sense of the invention comprises not only a fusion of two or more proteins but also the fusion of a protein with one or more peptides, e.g. a tat sequence. In a preferred embodiment, the fusion protein comprises a component combined with the haemoglobin or globin which promotes the absorption of the haemoglobin and/or globin by a neuronal, myocardial and/or skeletomuscular cell.

A further embodiment of the invention consists of the use of a nucleic acid which encodes at least one globin or one mutein or fusion protein thereof for the gene therapy of neurodegenerative and/or ischaemic diseases in maminals, e.g. in humans. Gene therapy here comprises all forms of therapy which introduce either globin sequences into the body or parts thereof or influence the formation of haemoglobins. For this, oligonucleotides, e.g. antisense or hybrid RNA-DNA oligonucleotides, with any modifications, which contain parts of the globin sequences, can be used. Viral constructs containing a globin sequence or parts thereof plus bare DNA containing a globin sequence or parts thereof can also be used.

Preferably the nucleic acid sequence used which encodes at least one globin or one mutein or fusion protein thereof is under the functional control of a heterologous regulatory element. This genetic regulation element is suitable for use in maminal systems, e.g. cell cultures from maminal cells. Neuronal, myocardial and/or skeletomuscular cells and cell lines are particularly preferred. The functional linking of the nucleic acid sequence with genetic regulation elements such as transcriptions and translation signals can, depending on the required application, lead to a raising or lowering of the gene expression. The recombinant nucleic acid constructs produced in this way are used then to transform host organisms.

In addition to these new regulation sequences, the natural regulation of the actual structural genes may still be present and may in some cases have been genetically modified so that the natural regulation has been switched off and the expression of the genes increased. The gene construct may also be structured more simply, i.e. no additional regulation signals are incorporated before the sequences and the natural promoter with its regulation is not removed. Instead, the natural regulation sequence is mutated in such a way that no regulation takes place any more and the gene expression is increased. Additional regulatory elements can also be incorporated at the 3' end of the nucleic acid sequences. The nucleic acid sequences for at least one globin or one mutein or fusion protein thereof may be contained in one or more copies in the gene construct or be localised in separate gene constructs. Advantageous regulation sequences for the method according to the invention are for example contained in promoters such as the cos, tac, trp, tet, trp-tet, Ipp, Iac, Ipp-Iac, laciq, T7, T5, T3, gal, trc, ara, SP6, I-PR or I-PL promoter, which are used advantageously in gram-negative bacteria. Further advantageous regulation sequences are contained for example in the gram-positive promoters such as amy and SPO2, in the yeast promoters such as ADC1, MFa, AC, P-60, CYC1, GAPDH or in maminal promoters such as CaM-Kinasell, CMV, Nestin, L7, BDNF, NF, MBP, NSE, beta globin, GFAP, GAP43, tyrosin hydroxylase, kainate receptor subunit 1, glutamate receptor subunit B. Basically, all natural promoters with their regulation sequences such as those mentioned above may be used. In addition, synthetic promoters can also be advantageously used.

These regulatory sequences aim to make possible the targeted expression of the nucleic acid sequences and protein generation. This can mean, for example, depending on the host organism, that the gene is only expressed or overexpressed after induction or that it is expressed and/or overexpressed iminediately. The regulatory sequences or factors can preferably positively influence and thus increase expression. Thus, an intensification of the regulatory elements at the transcription level may occur, by strong transcription signals such as promoters and/or enhancers being used. In addition, however, an intensification of the translation is also possible, by improving, for example, the stability of the mRNA. The term "enhancers" is used to mean DNA sequences which produce increased expression through an improved interaction between RNA polymerase and DNA. As further regulation sequences, the "locus control regions", "silencers" or part-sequences thereof could be mentioned as examples. These sequences may be advantageously used for a tissue-specific expression.

The invention also provides a gene therapy construct, comprising a nucleic acid sequence which encodes at least one globin or one mutein or fusion protein thereof, under the functional control of a heterologous regulatory element. A preferred embodiment envisages the linking of the nucleic acid sequence with a promoter, whereby the promoter will be 5' "upstream". Further regulation signals such as the 3'-located terminators or polyadenylation signals or enhancers can be functionally used in the nucleic acid construct. The term "gene therapy construct" is also used to mean complete vector constructs which are suitable for gene therapy. These vector constructs or vectors are used for expression in a suitable host organism. The gene therapy constructs according to the invention can also be incorporated into a host-specific vector which allows an optimum expression of the genes in the selected host. The expert is familiar with vectors, and they can be taken, for example, from the book "Cloning Vectors" (publ. Pouwels P. H. et al., Elsevier, Amsterdam-New York-Oxford, 1985). The term "vectors" includes not only plasmids but also all other vectors known to the expert such as phages, viruses such as SV40, CMV, baculovirus, adenovirus, sindbis virus, transposons, IS elements, phasmids, phagemids, cosmids, linear or circular DNA. These vectors can be replicated autonomously in the host organism or replicated chromosomally. Linear DNA is used preferably for integration into maminals.

To increase the expression of the nucleic acid sequences contained in the constructs according to the invention, the number of gene copies can, for example, be increased and/or the regulatory factors which positively influence gene expression can be intensified. An intensification of regulatory elements is carried out preferably at the transcription level through the use of stronger transcription signals such as promoters and enhancers. In addition, however, an intensification of the translation is also possible by, for example, the stability of the mRNA being improved or the reading efficiency of this mRNA at the ribosomes being increased. To increase the number of gene copies, the nucleic acid sequences or homologous genes can be incorporated for example into a nucleic acid fragment or into a vector which contains preferably the regulatory gene sequences assigned to the genes in question or which has a promoter activity with a similar effect. In particular, such regulatory sequences are used which enhance the gene expression. In addition, the gene therapy construct according to the invention can also be expressed in the form of fragments suitable for therapy or diagnosis. To generate the recombinant protein, vector systems or oligonucleotides can be used which extend the nucleic acids or the nucleic acid construct by certain nucleotide sequences and thus encode for changed polypeptides which are used for simpler cleaning. Hexahistidine anchors, for example, are known in the literature as "tags" of this type, as are epitopes which can be recognised as antigens of various antibodies (Studier et al., Meth. Enzymol., 185, 1990: 60-89 and Ausubel et al. (eds.) 1998, Current Protocols in Molecular Biology, John Wiley & Sons, New York).

The invention also provides a host cell which contains a gene therapy construct according to the invention. Transfected cell lines and transfected stem cells, especially embryonic and adult stem cells are preferred for cellular gene therapy processes (e.g. transplantation). However, basically all organisms are suitable as host cells which allow an expression of the nucleic acid sequences contained in the construct according to the invention. Host organisms are understood to be, for example, bacteria, fungi, yeasts, plant or animal cells. Preferred organisms are bacteria such as *Escherichia coli*, *Streptomyces*, *Bacillus* or *Pseudomonas*, eukaryotic microorganisms such as *Saccharomyces cerevisiae*, *Aspergillus*, higher eukaryotic cells from humans or animals, such as COS, Hela, HEK293, Sf9 or CHO cells. The combination of the host organism and the vectors which suit the organism, such as plasmids, viruses or phages such as, for example, plasmids with the RNA polymerase/promoter system, the phages I, Mu or other temperent phages or transposons and/or further advantageous regulatory sequences form an expression system. The term "expression system" is understood as being, for example, the combination of maminal cells such as CHO cells and vectors such as pcDNA3neo vector or HEK293 cells and CMV vector, which are suitable for maminal cells.

In addition, transgenic non-human animals which contain a gene therapy construct according to the invention are provided by the invention. These animals are genetically modified to the effect that they neuronally express a quantity of haemoglobin which is changed in comparison with normal animals (i.e. not transfected animals). This covers e.g. mice, rats, sheep, cows or pigs. Transgenic animals which have been genetically modified to the effect that their neuronal haemoglobin or parts thereof is lacking or has been modified can also be considered. The transgenic organisms can also be so-called "knock-out" animals. The transgenic animals can contain a functional or non-functional gene therapy construct according to the invention, alone or in combination with a functional or non-functional sequence which encodes for globins. A further embodiment is based on transgenic animals in whose germ cells or the totality or a part of the somatic cells, or in whose germ cells and the totality or a part of the somatic cells the gene therapy construct according to the invention has been modified by genetic methods or interrupted by the insertion of DNA elements. A further possibility for the use of a globin-encoding nucleotide sequence or parts thereof is the production of transgenic or "knock-out" or conditional or region-specific "knock-out" animals or specific mutations in genetically modified animals (Ausubel et al. (publ.) 1998, Current Protocols in Molecular Biology, John Wiley & Sons, New York and Torres et al., (publ.) 1997, Laboratory protocols for conditional gene targeting, Oxford University Press, Oxford). Using transgenic overexpression or genetic mutation (null mutation or specific deletions, insertions or modifications) through homologous recombination in embryonic stem cells, it is possible to produce animal models which provide valuable further information about the (patho-)physiology of the constructs according to the invention. Animal models made in this way can represent essential test systems for the evaluation of new therapeutic agents, especially for the testing of protective substances.

The following figures and examples elucidate the invention:

FIG. 1 shows in the form of a diagram the result of a transcription analysis in the brain of EPO-transgenic mice. The graphic presents the data of a DNA array hybridisation experiment. The points above the diagonal represent highly regulated gene products in the brain of EPO-transgenic animals.

FIG. 2 shows the result of an agarose gel electrophoresis of the RT-PCR products for haemoglobin messenger RNA. The picture of the agarose gel electrophoresis of the RT-PCR product for alpha globin shows a high expression of haemoglobin alpha messenger RNA in the brain of the six transgenic animals in comparison with wild type animals. This analysis is an end-point analysis and is therefore semi-quantitative.

FIG. 3 shows the result of a quantitative PCR for alpha globin from brain cDNA. The data represent pooled RNA from 6 brains (tg or wt).

FIG. 4 shows the result of a two-dimensional gel electophoresis from total brain extract from wild type and transgenic mice for haemoglobin proteins. With the application of the same quantity of total protein from a total brain extract, the comparison of the optical densities and volumes of the protein points produces mean induction factors of $2.68 \pm 0.29$ (n=6) for haemoglobin alpha and $2.59 \pm 0.37$ (n=6) for haemoglobin beta.

FIG. 5 shows a bar chart of the haemoglobin concentration, determined using the cyanohaemiglobin method, in the brain homogenate of 6 wild type and 6 transgenic mice. The concentrations were 0.029±0.012 mg/(dl brain homogenate) (n=6) for the transgenic and 0.011±0.006 mg/(dl brain homogenate) (n=6) for the wild type group.

FIG. 6 shows the results of an in-situ hybridisation for localisation of haemoglobin messenger RNA in the brain. Digoxigenin-labelled oligonucleotide probes specifically for haemoglobin were detected in mouse brain cryosections by anti-digoxigenin antibodies and made visible by a colour reaction. (A) shows the brain of a non-transgenic sibling animal, (B) shows the clearly stronger in-situ signals especially in the hippocampus, gyrus dentatus, cerebellum and cortex regions.

FIG. 7 shows the localisation of haemoglobin protein in the brain with DAF dye. A. Haemoglobin expression in the brain of mice (not transgenic). Signals can be seen in the hippocampus, the cerebral cortex and the paraventricular thalamic core. The expression locations of the haemoglobin protein correspond overall to the expression locations of the haemoglobin messenger RNA. B. and C.: Enlargements of the cerebellum and hippocampus, which show the strongest expression.

FIG. 7.1. Use of diaminofluorene dye for haemoglobin in the brain section of transgenic mice. Clear staining (black-blue) in the cerebral cortex (A) and hippocampus (B) can be seen (arrows).

FIG. 8 shows the localisation of haemoglobin protein in the brain in the hippocampus of wt and tg animals with DAF dye. A. Haemoglobin expression in the hippocampus of mice (not transgenic). B. The same region from a transgenic animal, line tg6. A much stronger, more specific signal can be seen than in the wild type animals.

FIG. 8.1. Comparison of use of diaminofluorene dye for haemoglobin in the brain (A) of a wild type mouse and (B) a transgenic mouse. In the brain of the transgenic mouse, there is a much higher expression (black-blue); the figure shows a section from the cerebral cortex.

FIG. 9 shows, in the form of a bar chart, the results of a quantitative PCR: alpha globin induction after intraperitoneal EPO administration. It shows the high regulation of alpha globin messenger RNA 6 and 24 hours after i.p. EPO administration in hemisphere halves of rats. si-6-1: sham-injected animal 6 h after NaCl administration; si-24-1: sham-injected animal 24 h after NaCl administration: ei-6-1/ei-6-2: EPO-injected animals 6 h after EPO administration, ei-24-1/ei-24-2: EPO-injected animals 24 h after EPO administration.

FIG. 10 shows, in the form of a bar chart, the results of a quantitative PCR: beta-globin induction after intraperitoneal EPO administration. It shows the high regulation of alpha globin messenger RNA 6 and 24 hours after i.p. EPO administration in hemisphere halves of rats. si-6-1: sham-injected animal 6 h after NaCl administration; si-24-1: sham-injected animal 24 h after NaCl administration: ei-6-1/ei-6-2: EPO-injected animals 6 h after EPO administration, ei-24-1/ei-24-2: EPO-injected animals 24 h after EPO administration.

FIG. 11 shows, in the form of a bar chart, the results of a test to confirm the high regulation of alpha globin by means of quantitative PCR. Alpha globin-specific primers were used to determine the relative regulation of mRNA compared with the contralateral hemisphere and sham-operated animals. The error bars show the standard deviation of a measurement over several dilution stages.

FIG. 12 shows, in the form of a bar chart, the results of a test to confirm the high regulation of beta globin by means of quantitative PCR. Beta globin-specific primers were used to determine the relative regulation of mRNA compared with the contralateral hemisphere and sham-operated animals. The error bars show the standard deviation of a measurement over several dilution stages.

FIG. 13 shows an RMDD strip section, showing alpha and beta globin. It shows the primarily identified strips, which were identified as alpha and beta globin, from mouse brains after MCAO with reperfusion at 2, 6 and 20 h. The ischaemic hemisphere, the contralateral hemisphere and sham-operated animals are shown in each case.

EXAMPLES

Example 1

Identification of Neuronal Alpha and Beta Globin as Erythropoetin-Regulated Genes Transgenic polyglobulic mice which overexpress human erythropoietin were produced as described (lines tg6 and tg21; Ruschitzka et al., 2000, Proc. Natl. Acad. Sci. USA 97, 11609-13; Wagner et al., 2001, Blood 97, 536-42; Wiessner et al., 2001, J. Cereb. Blood Flow Metab. 21, 857-64). C57BL6 wild type sibling animals were used as the control.

The mice were produced with a recombinant construct using methods with which the expert is familiar. This construct consisted of a PDGF promoter which causes an expression of the recombinant EPO particularly in neuronal cells (Sasahara et al., 1991, Cell 64, 217-27) and the encoding sequence for erythropoietin. Several transgenic lines were created, of which tg6 and tg21 were examined. Only tg6 showed a systemically increased EPO expression, which was proved by serum studies (Ruschitzka et al., 2000, loc. cit.). Line tg21 showed no increased systemic EPO level.

In the mice in line tg6, the increased systemic expression of EPO lead to a clear increase in the erythropoesis resulting in a polyglobuly up to a haematocrit of 0.8 and a clearly increased blood volume (up to 4.0 ml). In-vivo studies showed in the tg6 line a globally increased brain metabolism (cerebral glucose utilisation). The reasons for this could be either a generally increased neuronal activity or a chronic hypoxia. There were no indications of a generally increased neuronal activity, such as cramp attacks or high motor activity. The results therefore indicate chronic hypoxia. The generally lower cerebral blood flow in these mice also points in the same direction: A reduced cerebral blood flow also causes tissue hypoxia (Frietsch et al., 2001, JCBF 21, Suppl. 1, p. 17). Line tg21, in contrast, shows no marked phaenotypical features.

For the removal of the brain, the mice were anaesthetised with 0.8% isoflurane, 70% $N_2O$ and 29% oxygen. To exclude the possibility that the haemoglobin found in the tests could come from the blood, the test animals were perfused with a cold saline solution to wash the blood out of the blood vessels.

Figure 1:
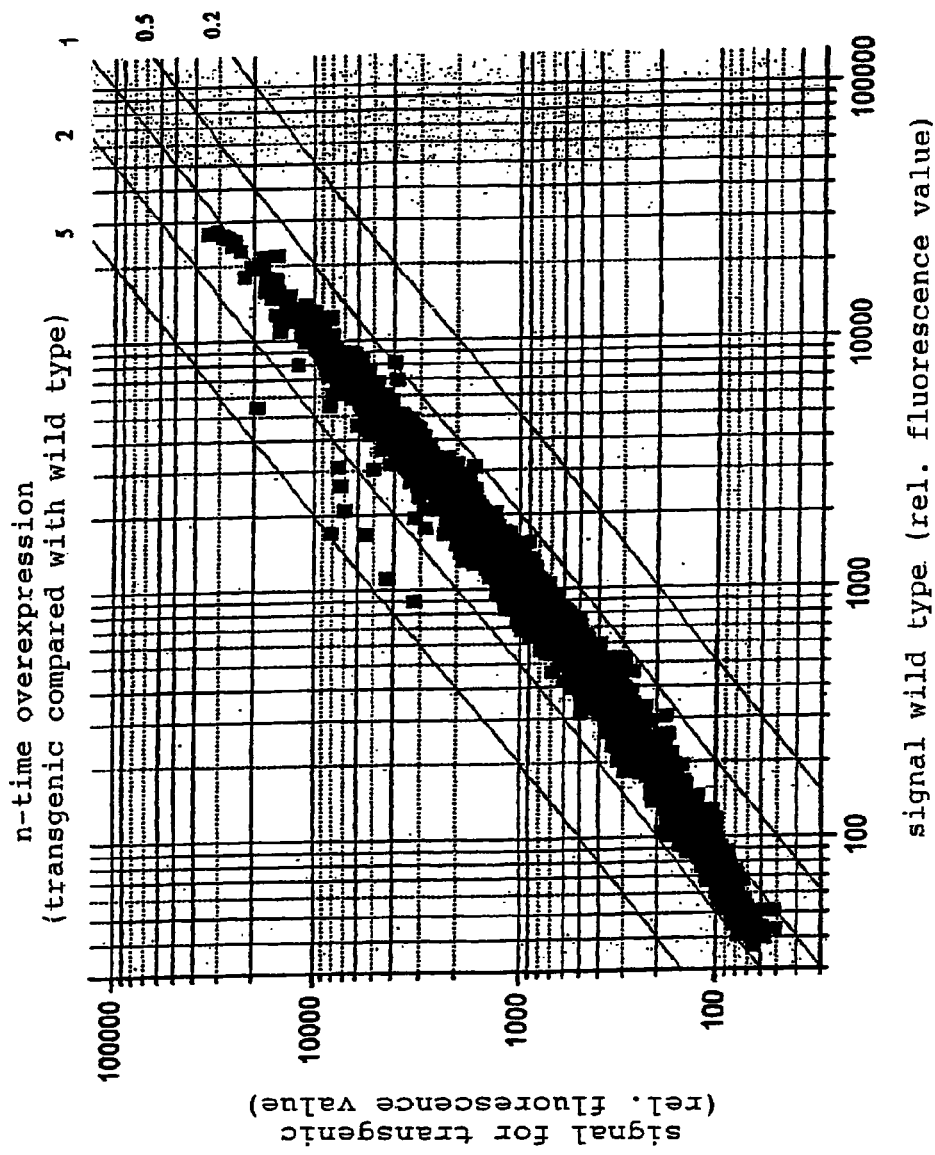

The brain of the transgenic mice overexpressing erythropoietin was removed under anaesthesia after transcardial perfusion and shock-frozen in liquid nitrogen. RNA was obtained using the method of Chomczynski and Sacchi (1987; Anal. Biochem. 162, 156-159). Afterwards, a hybridisation experiment with 2 transgenic and 2 litter mate controls was carried out on a mouse cDNA array ("Chip") (FIG. 1). The hybridisation experiment produced a series of highly regulated sequences. One sequence stood out, which seemed to be highly regulated in the animals of both line tg6 and line tg21. This sequence was identified through searching through public databases as alpha globin.

Example 2

Detection of Increased Haemoglobin Messenger RNA in the Brain of Transgenic Mice Overexpressing Erythropoietin To measure the haemoglobin messenger RNA, the semi-quantitative RT-PCR was used on a LightCycler (Roche, Mannheim, Germany). Quantification was carried out by comparing the relative fluorescence of the sample with a standard curve for cyclophilin.

Total RNA was isolated from the mouse brain with the RNeasy extraction kit in accordance with the manufacturer's instructions (Qiagen, Santa Clarita, Calif., USA). The RNA concentration was determined photometrically and the quality of the total RNA was assessed via agarose gel electrophoresis. The RNA was kept at −80° until use.

After reverse transcription with Superscript II (Invitrogen-Life Technologies, Carlsbad, Calif., USA), the reaction products were relatively quantified by real-time online PCR using LightCycler technology. For this, total RNA samples from the brain of three wild type mice and three transgenic mice were used. The specific sequences of the oligonucleotide primers for cyclophilin were

```
5'-ACCCCACCGTGTTCTTCGAC-3'   (SEQ ID NO:1)
``` for the forward primer and

```
5'-CATTTGCCATGGACAAGATG-3'   (SEQ ID NO:2)
``` for the reverse primer with an annealing temperature of 60 C. and for haemoglobin alpha

```
5'-GGTGCCCTGTCTGCTCTG-3'     (SEQ ID NO:3)
``` for the forward primer and

```
5'-GGCAGCTTAACGGTACTTGG-3'   (SEQ ID NO:4)
``` for the reverse primer at 55 C. annealing temperature.

Figure 2:
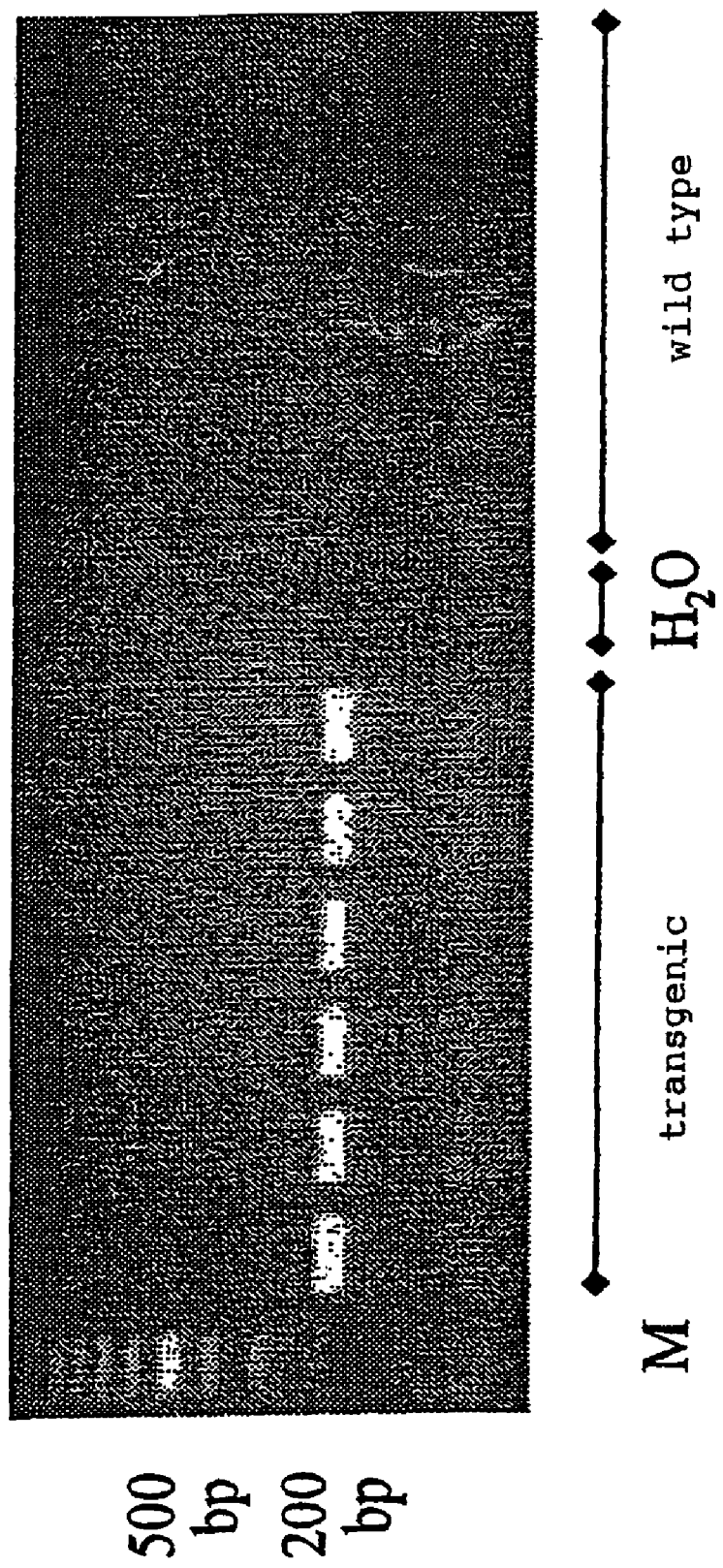
Figure 3:
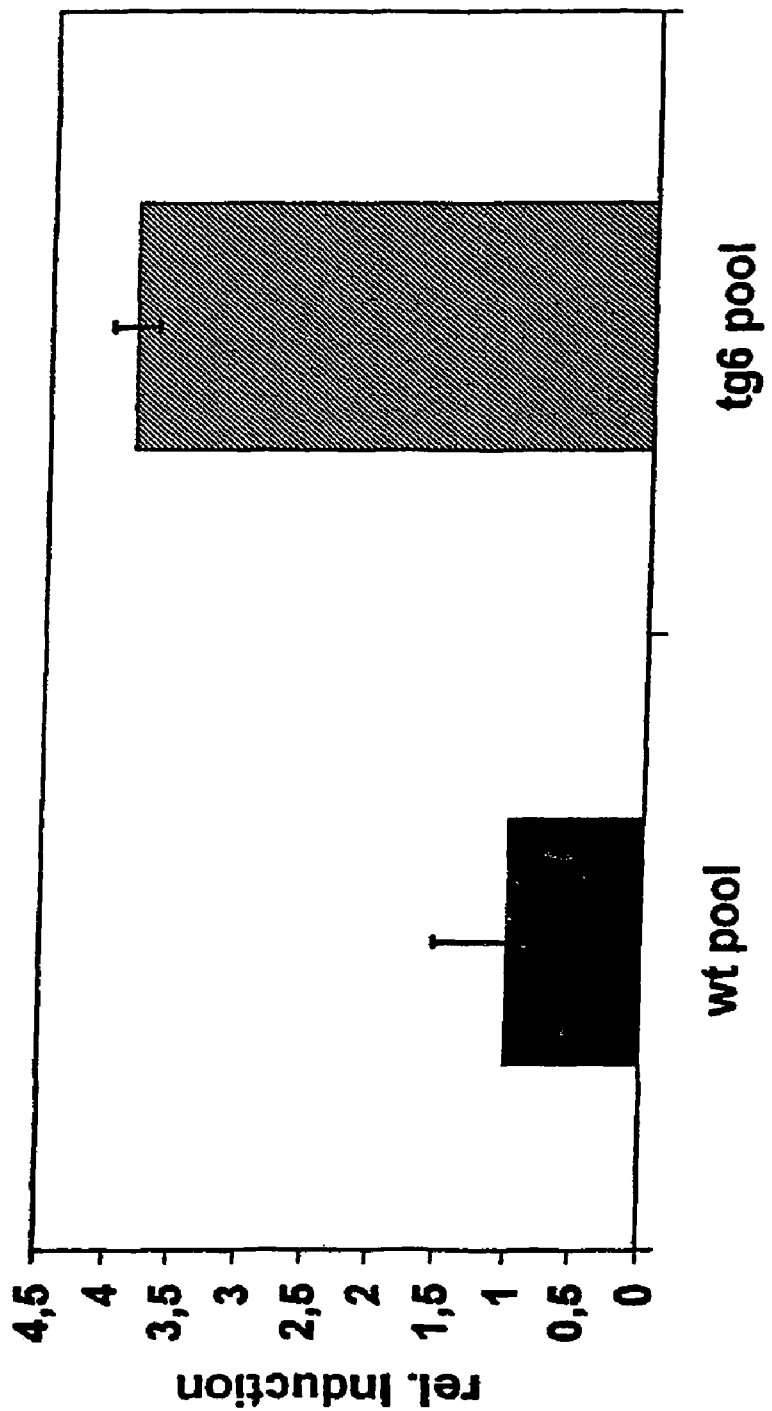

For the quantification, serial cDNA dilutions of 1:3, 1:9, 1:27, 1:81 and 1:243 were amplified according to the following scheme: Initial denaturing 5 min at 94° C., amplification over 50 cycles consisting of 5 s denaturing at 94° C., 10 s annealing at 55° C. or 60° C.—depending on the specific primer (see above)—and 30 s extension at 72° C. At the end of each cycle, the fluorescence of each sample was measured at 80° C. for 10 s. The specificity of the reaction product was determined by agarose gel electrophoresis (FIG. 2) and melting curve analysis (not shown). Each PCR reaction produced exactly one reaction product.

Figure 8:
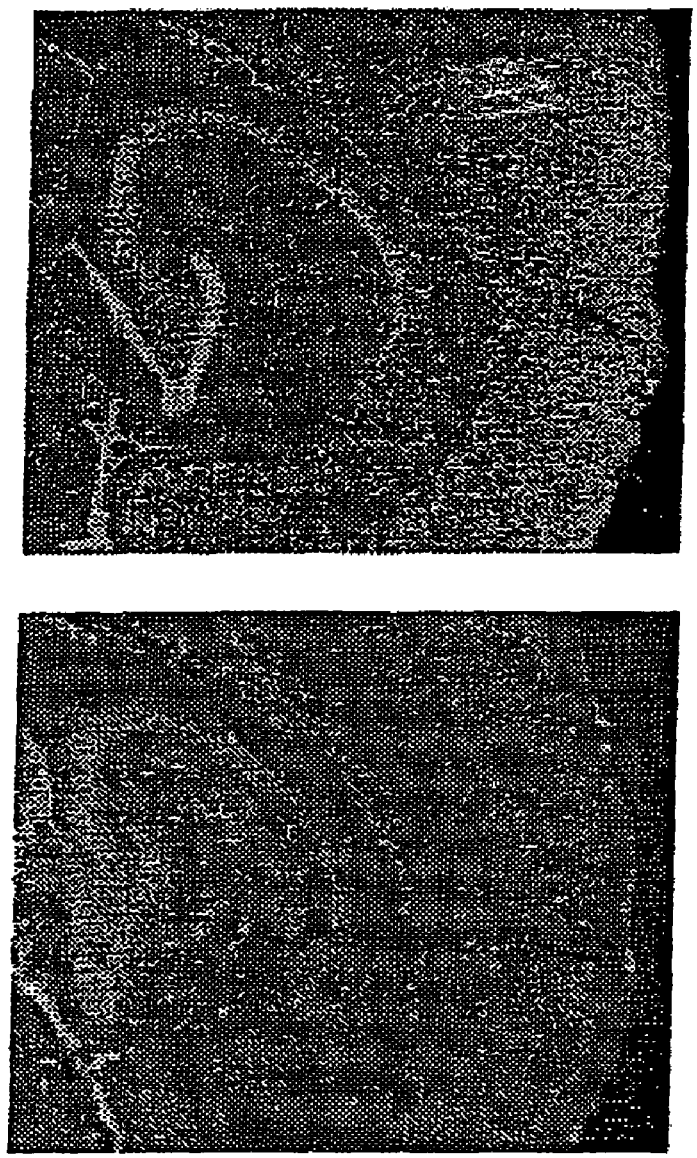

For the quantification, the logarithmic phase of the PCR reaction was used. An asymptote is laid through the corresponding curve. For haemoglobin, an almost parallel rise in the family of straight lines occurred, so that the rises in these curves could be used for comparison with the standard curves for cyclophilin. Mean values±standard deviation were determined for each cDNA dilution from the normalised PCR product (FIG. 8). The quantitative differences obtained in this way correspond to relative changes in the RNA expression in the transgenic and wild type animals. All the reactions led to a single reaction product (indicated by a single peak in the melting curve at around 90° C. for the transgenic and wild type mice). The mean induction factor for haemoglobin alpha was 3.86±0.18 (n=3).

Example 3

Increase in Haemoglobin Protein in the Brain of Transgenic Mice Overexpressing Erythropoietin Through semi-quantitative two-dimensional gel electrophoresis, changes in the expression of haemoglobin alpha and haemoglobin beta were measured in the brain of six transgenic tg6 mice and six wild type mice.

For the two-dimensional gel electrophoresis, the brain tissue was homogenised in 2 ml sample buffer consisting of 40 minol/l tris, 7 mol/l urea, 2 mol/l thiourea, 4% (w/v) CHAPS, 10 minol/l DTT and 1 minol/l EDTA and centrifuged for 45 min at 100,000×g. The protein content of the samples was determined according to the Bradford method (Bradford, 1976, Anal. Biochem. 72, 248-254).

The two-dimensional gel electrophoresis was carried out according to standard protocols (Görg et al., 2000, Electrophoresis 21, 1037-1053). Samples of 500 µg were applied for isoelectric focussing on non-linear pH 3-10 gradient IEF gel strips (Amersham Bioscience, Freiburg, Germany). After 6 h swelling time, 30 V were applied for 6 h, followed by 500 V for 1 h and 1000 V for 1 h. After this, the voltage was increased to 8000 V and kept constant for 10 h. This produced 81680 Vh on the IPGphor IEF system for the isoelectric focussing. Separation in the second dimension was completed in 12.5% polyacrylamide gels in the presence of 10% SDS. 30 mA were applied to the gels (180×200×1.5 $min^3$) for 30 min and 100 mA for around 4 h in a water-cooled vertical eletrophoresis chamber (OWL Scientific, Woburn, Mass., USA). The gels were dyed with silver nitrate according to a modified protocol (Blum et al., 1987, Electrophoresis 8, 93-99) in order to make the proteins visible. This method is compatible with a subsequent mass spectrometry.

Figure 4:
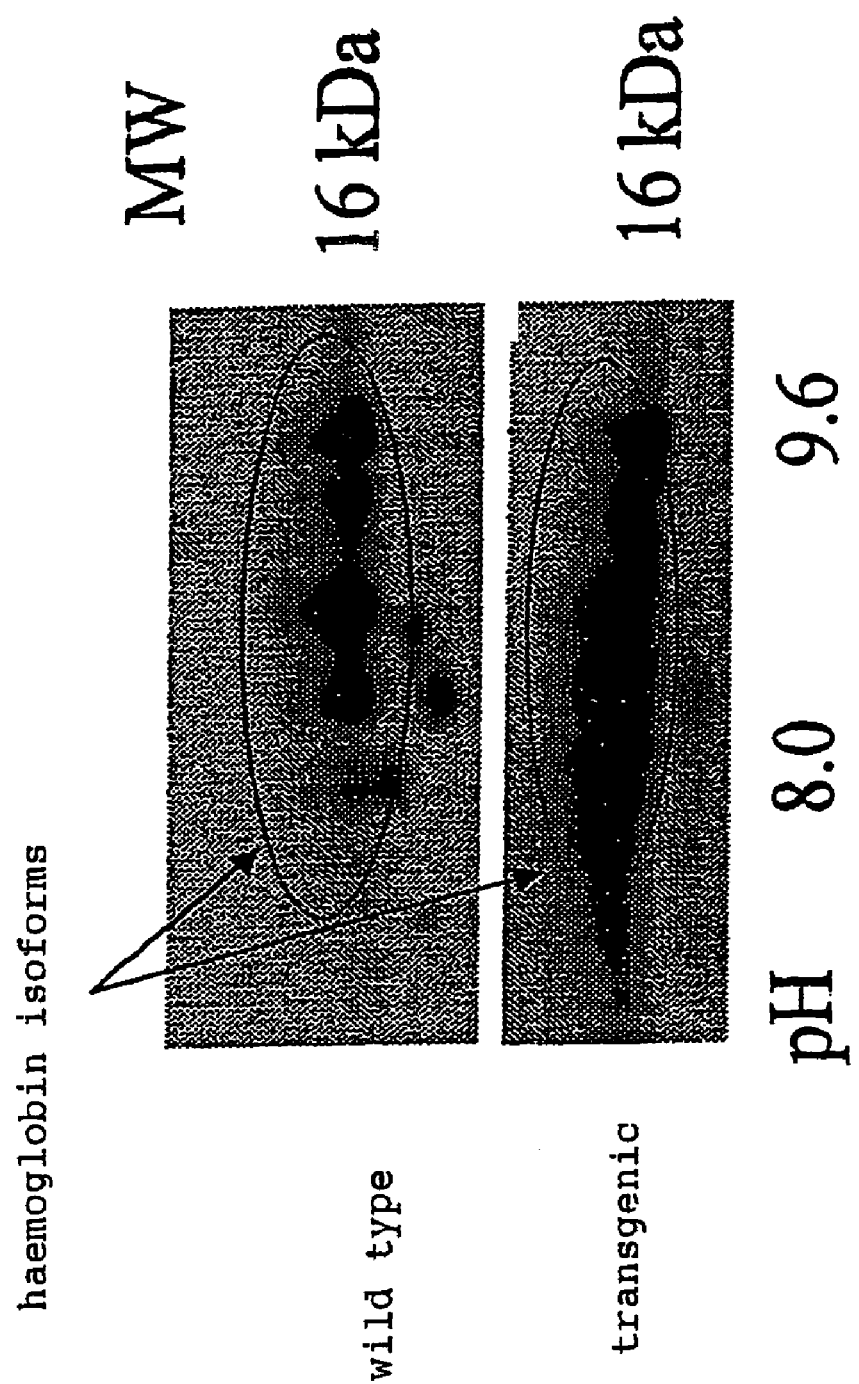

The gels were then scanned in and the images measured densitometrically with the special software Phoretix 2D Professional (Nonlinear Dynamics Ltd., Newcastle-upon-Tyne, UK). After a background correction, the protein points for haemoglobin alpha and haemoglobin beta were measured by optical density and volume. Mean values±standard deviations from six transgenic animals were compared with those from six wild type animals with the t test according to Student. A p value <0.05 was accepted as the significance limit. The proteins were identified by mass spectrometry (ZMBH, Center of Molecular Biology Heidelberg, Heidelberg, Germany). The mean induction factors were 2.68±0.29 (n=6) for haemoglobin alpha and 2.59±0.37 (n=6) for haemoglobin beta (FIG. 4).

Figure 5:
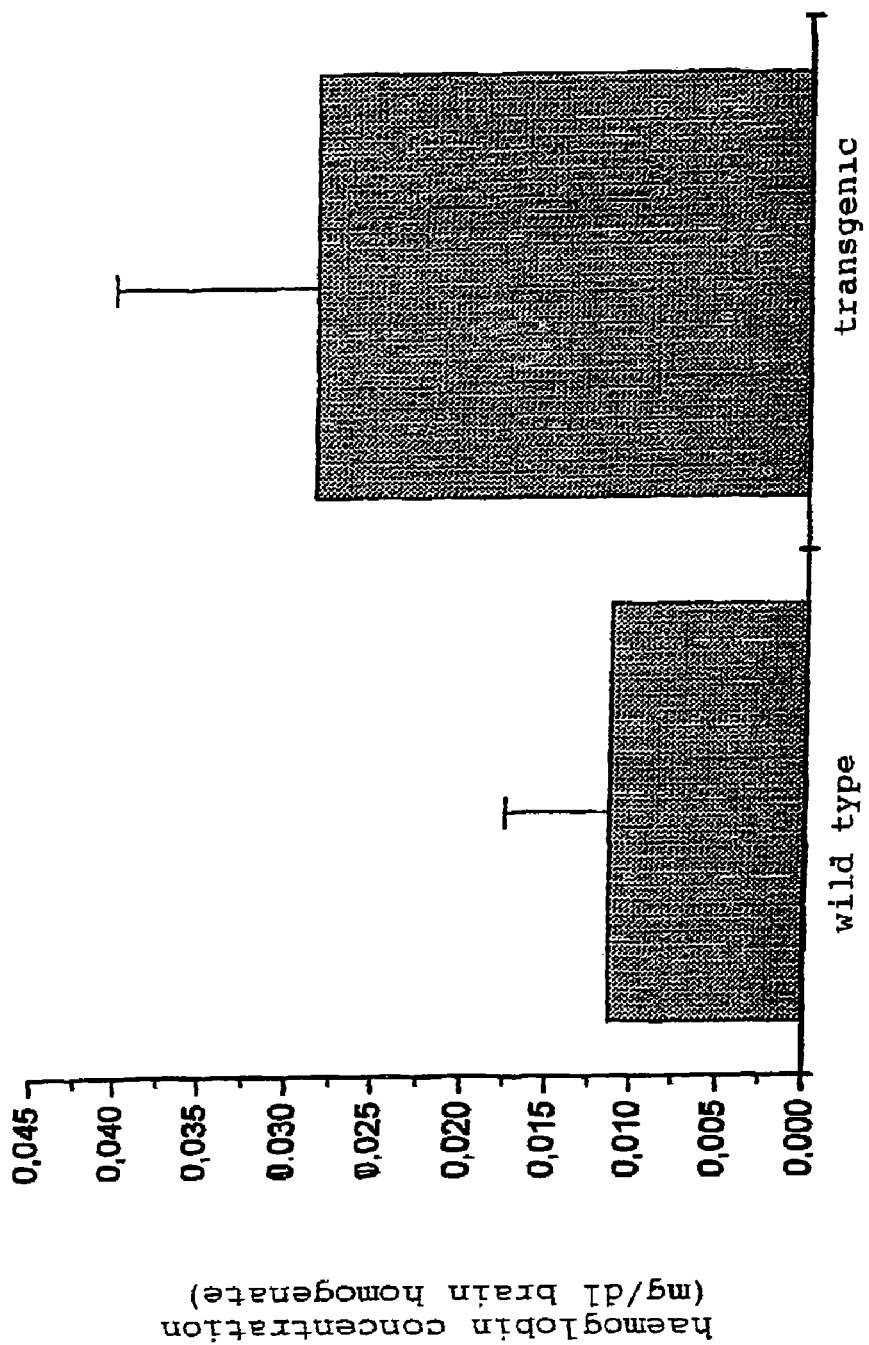

In addition, using the rapid cyanhaemiglobin method (van Kampen and Zijistra, 1961, Clin. Chim. Acta, 538-544), the absolute haemoglobin concentration in the brain of six transgenic and six wild type mice was measured. For this, 20 µl of the corresponding brain homogenate samples were added to 5 ml of a transformation solution consisting of 200 mg/l potassium hexacyanoferrate, 50 mg/l potassium cyanide, 140 mg/l potassium dihydrogen phosphate and 0.05% (v/v) Triton X-100 and incubated for at least 5 min at room temperature. The extinction was then measured at 546 nm and multiplied by 36.7 to obtain the concentration in g/dl. The concentrations were 0.029±0.012 mg/(dl brain homogenate) (n=6) for the transgenic and 0.011±0.006 mg/(dl brain homogenate) (n=6) for the wild type group (FIG. 5).

Example 4

Localisation of Haemoglobin Messenger RNA in the Brain of Transgenic Mice Overexpressing Erythropoietin The expression locations for haemoglobin alpha messenger RNA were made visible by in-situ hybridisation using digoxigenin-labelled oligonucleotides. Specific bonds were made visible in mouse brain cryosections through incubation with an anti-digoxigenin antibody to which alkaline phosphatase is bound.

The in-situ hybridisation was carried out as described for digoxigenin-labelled oligonucleotide probes (Wisden and Morris, 1994, In situ hybridization protocols for the brain, Academic Press, London; San Diego). For this, 10 µm thick cryosections were fixed in ice-cold paraformaldehyde for 5 min, washed for 5 min in 1 X PBS (130 mM NaCl, 7 mM Na$_2$HPO$_3$, 3 mM NaH$_2$PO$_3$), dehydrated for 5 min in 70% (v/v) ethanol and stored in 96% (v/v) ethanol. The hybridisation probe for haemoglobin had the sequence (SEQ ID NO:5)
5'-CTTACATCAAAGTGAGGGMGTAGGT-3' and was labelled with digoxigenin at the 3' end (MWG-Biotech, Ebersberg, Germany). The probe was diluted in hybridisation buffer consisting of 5 g dextran sulphate dissolved in 25 ml ion-free formamide, 10 ml 20 X SSC (3 M NaCl, 0.3 M sodium citrate, pH 7.0) and sterile, RNase-free water to 50 ml. This gave a final concentration of 30 ng probe per section. Hybridisation was carried out at 42 C. over night in a water bath in an incubation chamber which was kept moist with 1:1 formamide at 4 X SSC. The sections were washed the next day in 1 X SSC for 10 min at room temperature (RT), 1 X SSC for 30 min at 60 C., 1 X SSC for 1 min at RT and 0.1 X SSC for 1 min at RT.

The sections were then incubated twice for 10 min in detection and wash buffer (150 min NaCl, 0.100 min tris-HCl, pH 7.5) and unspecific antibody bonds were blocked by 2% (v/v) normal sheep serum in detection and wash buffer with 0.1% (v/v) Triton X-100 for 30 min. After this, the sections were incubated for 4 h in an anti-digoxigenin antibody solution (Roche, Mannheim, Germany, 1:200 in block solution).

The sections were washed twice 10 min in detection and wash buffer and the pH value compared by iminersion for 10 min in substrate buffer (100 min NaCl, 50 min MgCl$_2$, 100 min tris-HCl, pH 9.5). The colour reaction was developed with BCIP/NBT for 2-24 hours until a sufficient colouration had appeared. The reaction was stopped with 10 min tris-HCl, pH 8.1 min EDTA and the sections embedded for light microscopy. For the control experiments, the sections were incubated either without oligonucleotide or without antibody.

Figure 6:
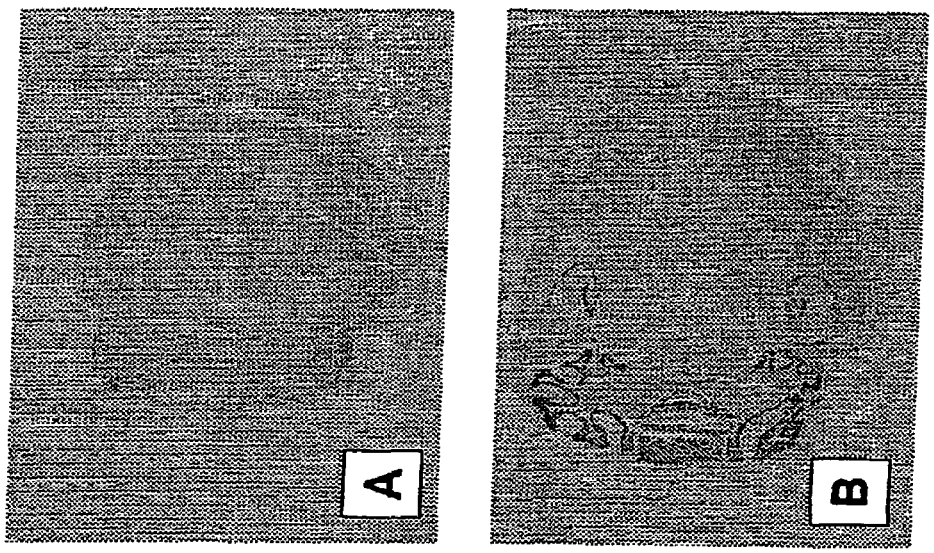

Bound antibodies produced a colour signal with BCIP/NBT as the substrate in the hippocampus and the cerebellum of the test animals, whereby the signals in the transgenic animals were stronger than in the wild type animals. Control experiments without oligonucleotide and without antibody showed a normal background colouring (FIG. 6). There is prominent expression in the granular layer of the cerebellum, in the Gyrus dentatus, in all areas of the hippocampus, in the habenulae and their cominissure. In addition, there were weaker, distributed signals in the cortex, striatum and thalamus compatible with neuronal expression. There were no signals in the corpus callosum and other areas with white substance.

Example 5

Localisation of Haemoglobin Protein in the Brain of Transgenic Mice Overexpressing Erythropoietin Haemoglobin protein was made visible by staining of cryosections with 2.7 diaminofluorene (DAF) in dark field microscopy. A protocol for the DAF staining was adapted for 10 µm cryosections (Worthington et al., 1987, Exp. Hematol. 15, 85-92). The sections were fixed for 2 min in ice-cold acetone and air-dried. The cell membranes were made permeable by triple washing in 200 min tris-HCl, pH 7.0, with 0.2% Tween-20 and the sections were incubated for 15 min at room temperature in a mixture of 100 µl 11% (w/v) DAF in 90% acetic acid, 100 µl 30% (w/v) H$_2$O$_2$ and 10 ml 200 min tris-HCl, pH 7.0. Afterwards, the sections were examined in the dark field microscope.

Figure 7:
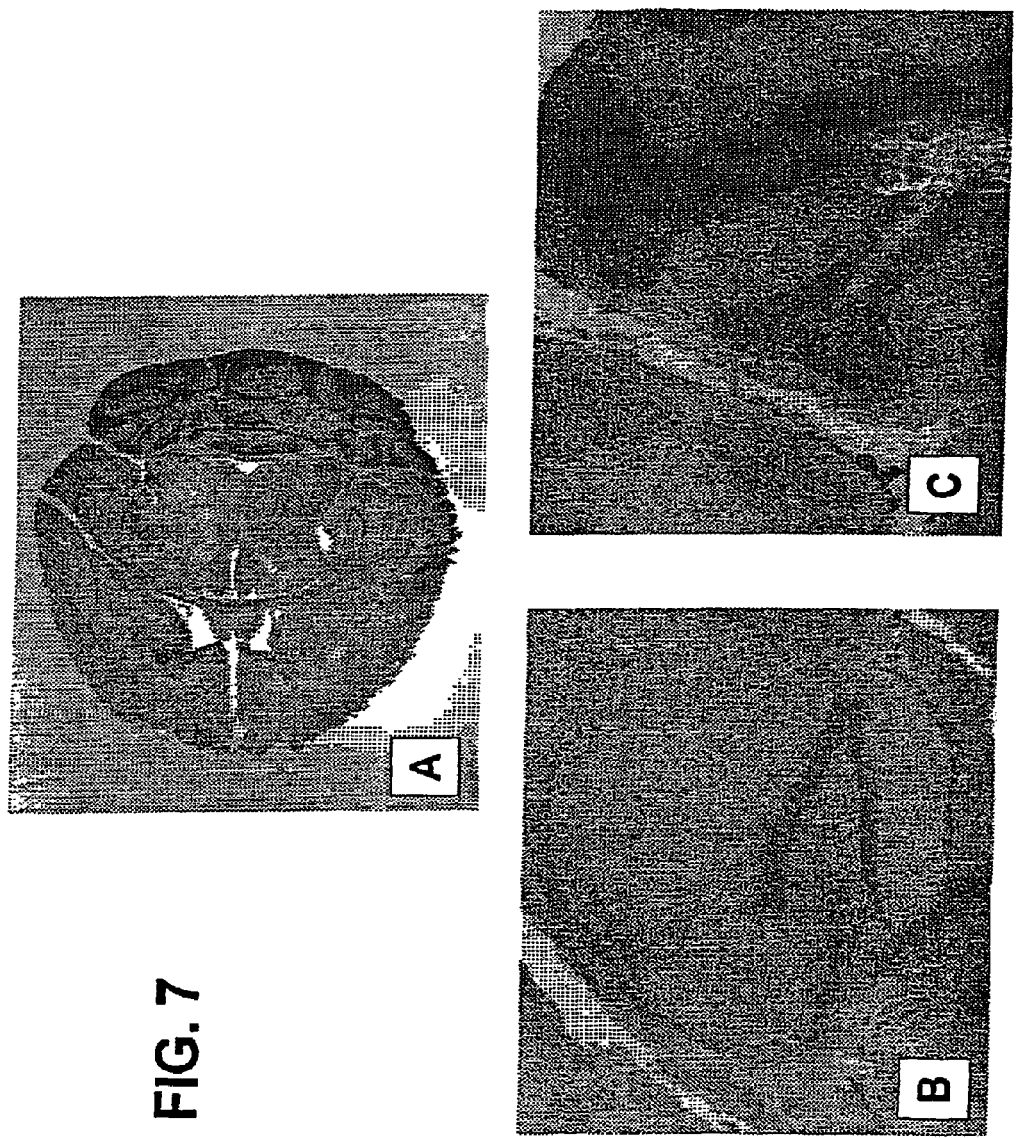

A clear staining appeared in the hippocampus, the cerebral cortex and the paraventricular core of the thalamus (FIG. 7). The expression locations for the haemoglobin protein correlate with the expression locations for the haemoglobin messenger RNA. DAF-stained sections of the hippocampus of wild type (A) and transgenic (B) animals (FIG. 8) showed a clearly stronger and more specific signal in the case of the latter.

To optimise the staining, additional experiments were carried out in which the incubation time in DAF buffers (1% (w/v) DAF in 90% acetic acid, 100 µl 30% (w/v) H$_2$O$_2$ and 10 ml 200 min tris-HCl, pH 7.0) was increased from 15 min to 60 min. FIGS. 7.1 and 8.1 show more clearly the localisation of haemoglobin and the differences between wild type and EPO-transgenic mice respectively.

Example 6

Detection of the Direct Induction of Haemoglobin by Erythropoietin

The induction of haemoglobin expression in mice which overexpress transgenic erythropoietin can be traced in principle to various effects of erythropoetin. It could be that the overexpression of EPO in early development stages of the mouse leads, because of a changed development program for the neurones, e.g. the hippocampal neurones, to a constitutive increased expression of haemoglobin. It could also be that only the long-term (over months) overexpression of EPO causes this effect, e.g. via more complex intermediate indirect mechanisms. To show the direct effect of EPO on the neuronal haemoglobin expression, the rats were given erythropoetin intraperitoneally and intracerebrally and the mRNA expression of alpha and beta globin in the brain was determined by quantitative PCR 6 or 24 hours after administration. The following doses were used here: 50 μl EPO solution in the dorsal hippocampus area (roughly in the area of the CA3 subregion) with a dose of 25 units (U). This was carried out for 4 rats; 2 of the rats were killed after 6 hours, and 2 after 24 hours. Sham-treated animals were also prepared.

RNA was obtained from the brain hemispheres and from the cerebellum for both the right and left hemisphere. Injection was into the right hemisphere by means of a stereotactic device. The injection location was verified using Evans-Blue injections. For the intraperitoneal injection, a dose of 5000 u/kg was administered; this was also done for 2 animals in each case and for the 6 and 24 h timings. The times were selected on the basis of the probability of the detection of an mRNA regulation through the direct effect of EPO. Once again, corresponding sham-injected animals were prepared.

After obtaining the RNA (Chomczynski and Sacchi, loc. cit.) followed by purification using Qiagen RNA_easy columns according to the manufacturer's instruction, cDNA was obtained using oligo-dT primers and Superscript II-Reverser transcriptase, followed by purification via Qiagen columns (cDNA purification protocol). Quantitative PCR was carried out using the LightCycler system (Roche, Mannheim, Germany), as already described above. Alpha and beta globin were quantified relatively against cyclophilin. The primers used were:

human ischaemic stroke. To bring about the focal cerebral ischaemia, the so-called thread model was used in which a coated nylon thread is pushed through the *A. carotis* interna to the outlet of the *A. cerebri* media and induces an ischaemic stroke (Clark et al., 1997, Neurol. Res. 19, 641-648).

To bring about a focal cerebral ischaemia in c57/bl6 mice (Charles-River WIGA, Sulzfeld, Germany), 3-month old mice were used. After inducing an inhalation narcosis (70% $N_2O$, 30% $O_2$, 0.8-1% halothane), a 5-0 prolene thread (Ethicon, Norderstedt) coated with 0.1% poly-L-lysin was pushed via the *A. carotis* externa into the A. carotis interna to the outlet of the *A. cerebri* media. The correct position of the thread is displayed by a decline in the laser Doppler signal (Perimed, Järfälla, Sweden) to 10-20% of the initial signal. After carrying out this operation and if applicable determination of additional physiological parameters (blood pressure, pulse, blood gases, blood glucose), the mice wake up from the narcosis. After certain occlusion times, the mice are subjected to narcosis again and the thread is pulled back. This causes a reperfusion of the tissue. After certain reperfusion times, the mice are killed by their necks being broken. The brain is prepared iminediately and frozen on dry ice. In the present

```
alpha globin: Primer rm_a_glob_s: 5'-GGGAAGATTGGTGGCCATGGTG-3', Tm 59      (SEQ ID NO:6)
              Primer rm_a_glob_a: 5'-GGCAAGGAATTTGTCCAGAGAGGC-3', Tm 59    (SEQ ID NO:7)

beta globin:  Primer rm_b_glob_s: 5'-CTGACTGATGCTGAGAAGGCTGCT-3', Tm 59    (SEQ ID NO:8)
              Primer rm_b_glob_a: 5'-TCCAGCCACCACCTTCTGGAAG-3', Tm = 59    (SEQ ID NO:9)

Cyclophilin:  5'-ACCCCACCGTGTTCTTCGAC-3' for the forward primer            (SEQ ID NO:1)
              and 5'-CATTTGCCATGGACAAGATG-3' for the reverse primer.           (SEQ ID NO:2)
```

Figure 9:
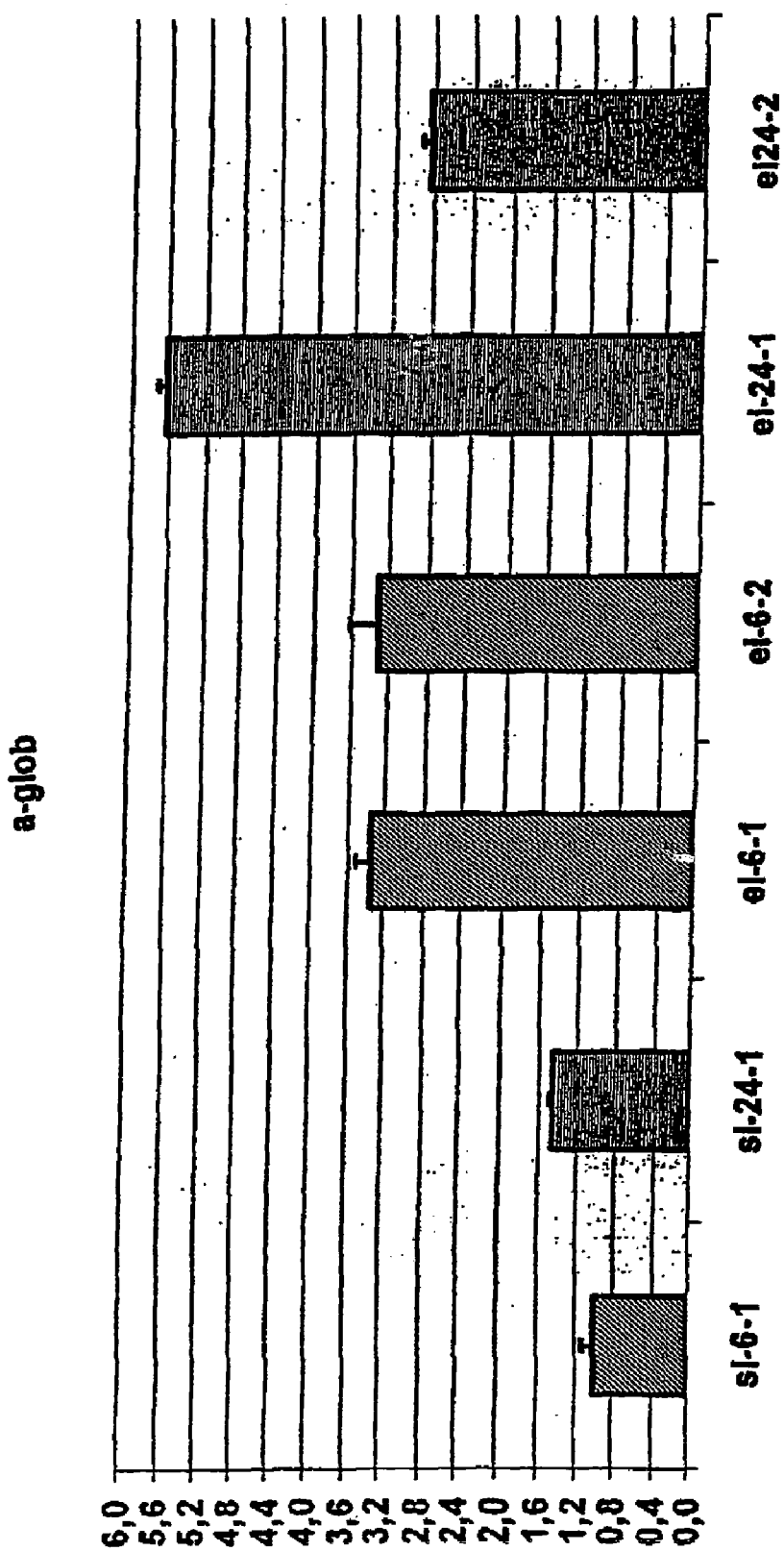
Figure 10:
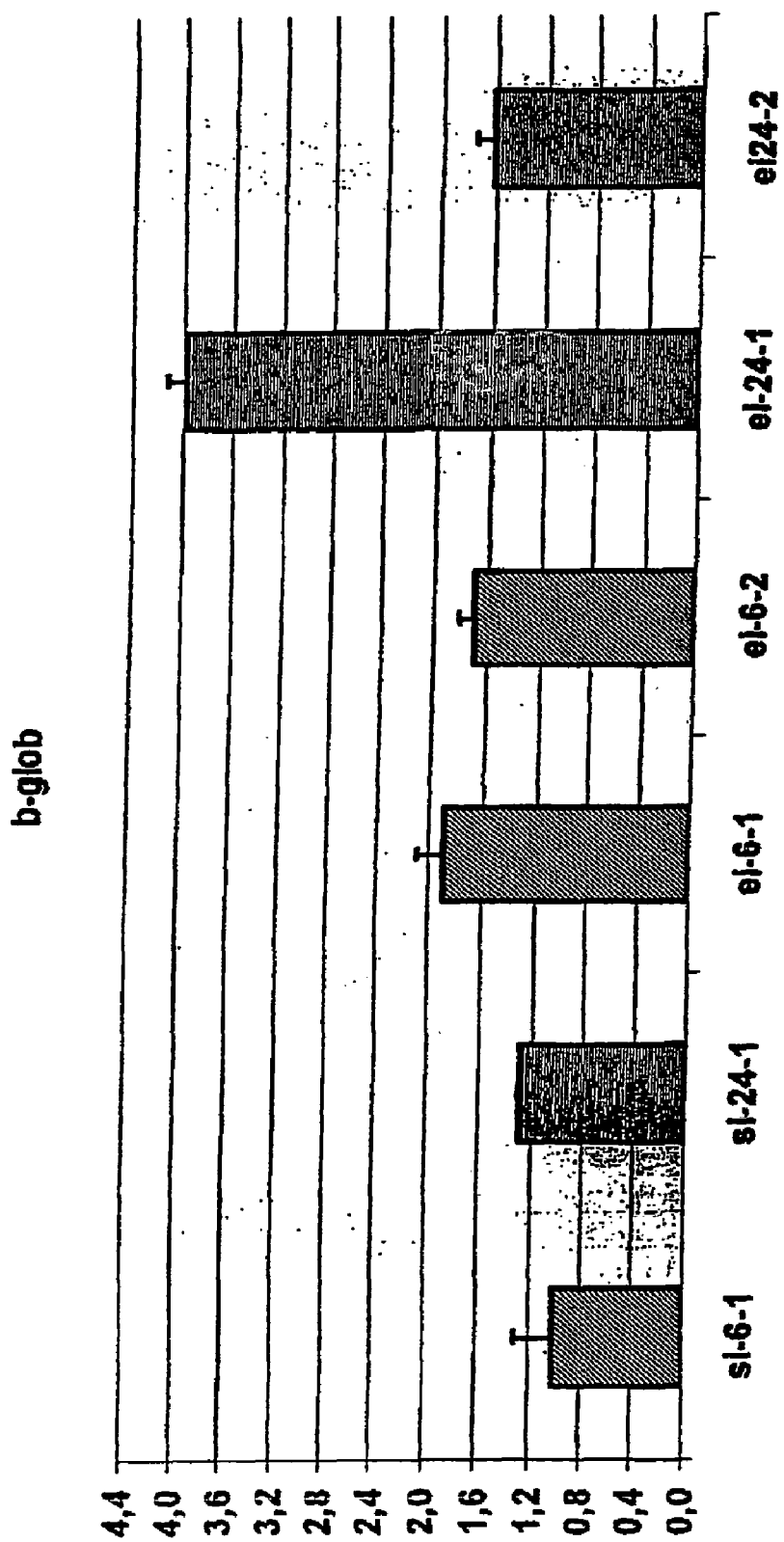

There was in each case a significant increase in alpha and beta globin in the intraperitoneally treated mice, which was in each case in the range of 2-4 times (see FIG. 9 and FIG. 10). This result clearly proves that the effect of EPO on haemoglobin expression is at least for the most part not a development phenotype and that the effect is effective in the short term and is therefore probably direct.

Example 7

Identification of Alpha and Beta Globin as Ischaemia-Induced Gene Products

The animal model of the focal cerebral ischaemia (middle cerebral artery occlusion, MCAO) represents a model for the case, occlusions were carried out for 90 min and reperfusions for 2 h, 6 h and 20 h.

1) Preparation of mRNA from the Brains and Detection of Haemoglobin Messenger RNA The method laid down by Chomczynski and Sacchi (loc. cit.) was applied, followed by a further purification using RNA purification columns (RNAeasy, Qiagen) in accordance with the manufacturer's instructions.

For the quantification of the mRNA regulation by cerebral ischaemia (MCAO model) the method described in Example 2 was adopted, but beta globin was also determined here. The primers used have the following sequence (identical for mouse and rat):

```
Alpha globin: Primer rm_a_glob_s: 5'-GGGAAGATTGGTGGCCATGGTG-3', Tm 59.degree.    (SEQ ID NO:6)
              and Primer rm_a_glob_a: 5'-GGCAAGGAATTTGTCCAGAGAGGC-3', Tm 59.degree.  (SEQ ID NO:7)

Beta globin:  Primer rm_b_glob_s: 5'-CTGACTGATGCTGAGAAGGCTGCT-3', Tm = 59.degree. (SEQ ID NO:8)
              Primer rm_b_glob_a: 5'-TCCAGCCACCACCTTCTGGAAG-3',   Tm = 59.degree. (SEQ ID NO:9)
```

Figure 11:
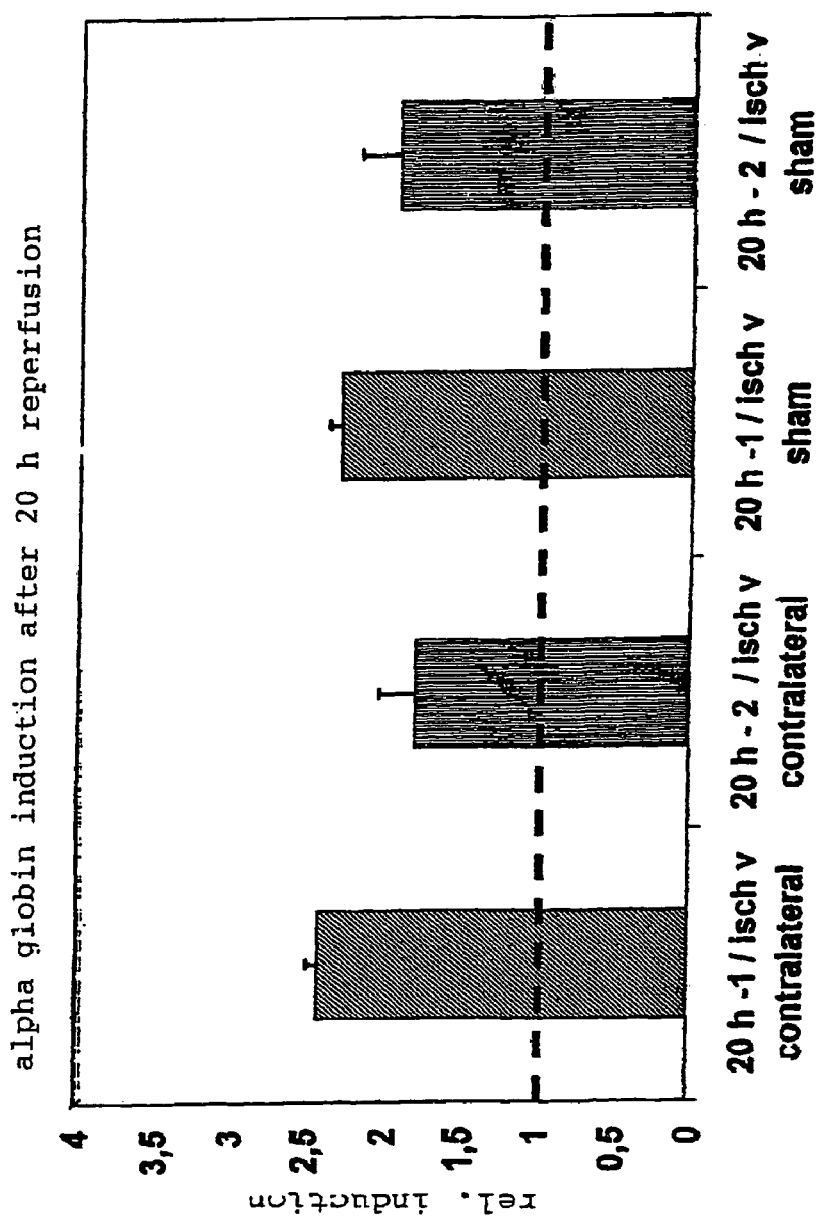
Figure 12:
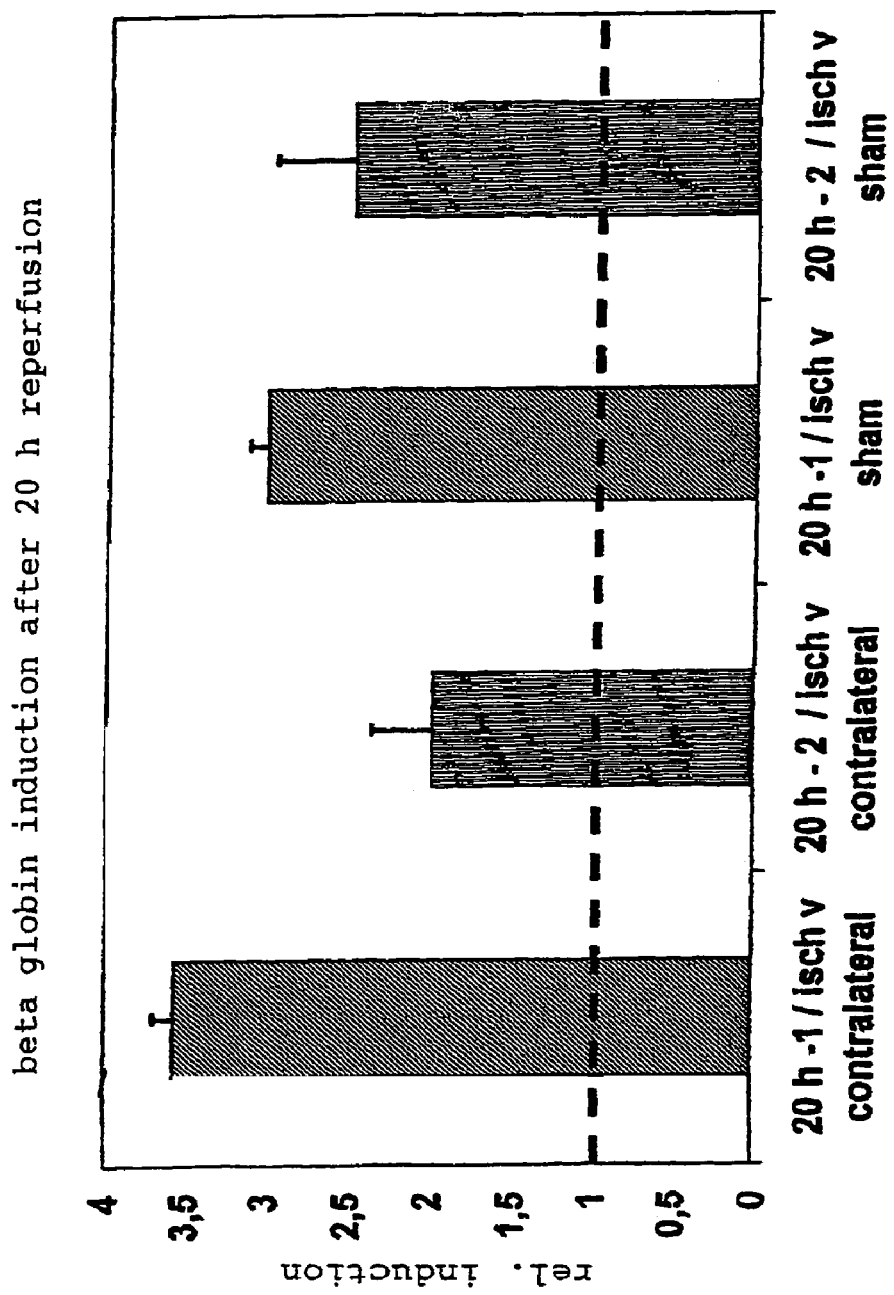

There were induction factors (ischaemic against contralateral hemisphere) for alpha globin of 2.41±0.07 and 1.78±0.24 in two animals with MCAO and 20 h reperfusion (FIG. 11). For beta globin, there were induction factors of 3.56±0.12 in one animal and 1.97±0.37 in a second (FIG. 12). In comparison with the sham-operated animals, there were comparable values.

2) Execution of the RMDD (Restriction Mediated Differential Display) Protocol

Figure 13:
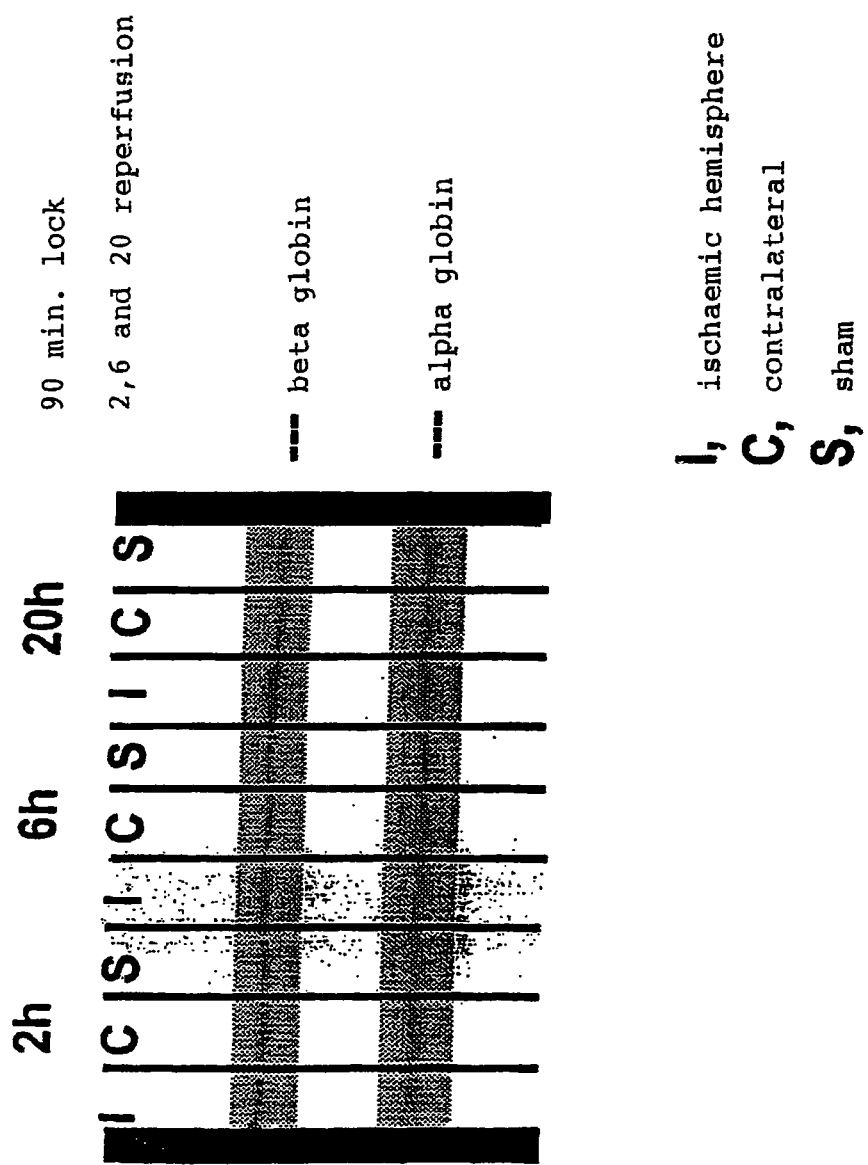

Basically the procedure described in EP 0 743 367 A 2 and U.S. Pat. No. 5,876,932 was followed, with the amendment that 2 ug polyA-RA was used for the first strand synthesis. After the first strand synthesis, second strand synthesis and restriction digestion have been carried out, an adapter ligation is carried out with adapters. After PCR amplification with adapter and cDNA primers, the amplification products are loaded onto a denaturing gel and blotted onto a nylon membrane (GATC, Konstanz, Germany). The biotin-marked strips are visualised using a standard streptavidin peroxidase reaction (Roche Molecular Biochemicals, Mannheim, Germany). PCR samples from the ischaemic and contralateral hemispheres together were applied to the gel in each case (24 h MCAO right and left and 90 min MCAO right and left). Strips of different intensity in the right or left hemisphere are cut out and a reamplification of the corresponding PCR product is carried out. The amplified products obtained are cloned in the TOPO TA Vector pcDNA 2.1 (Invitrogen, Carlsbad, Calif., USA) and sequenced with T7 and M13rev primers (ABI 3700 capillary electrophoresis sequencer, PE Applied Biosystems, Foster City, Calif., USA). The sequences obtained are compared with the EMBL database. This showed sequences for alpha and beta globin (FIG. 13).

Example 8

Detection of Direct Haemoglobin Induction in the Brain Through One-Off Erythropoetin Injection (Intraperitoneal)

Figure 14:
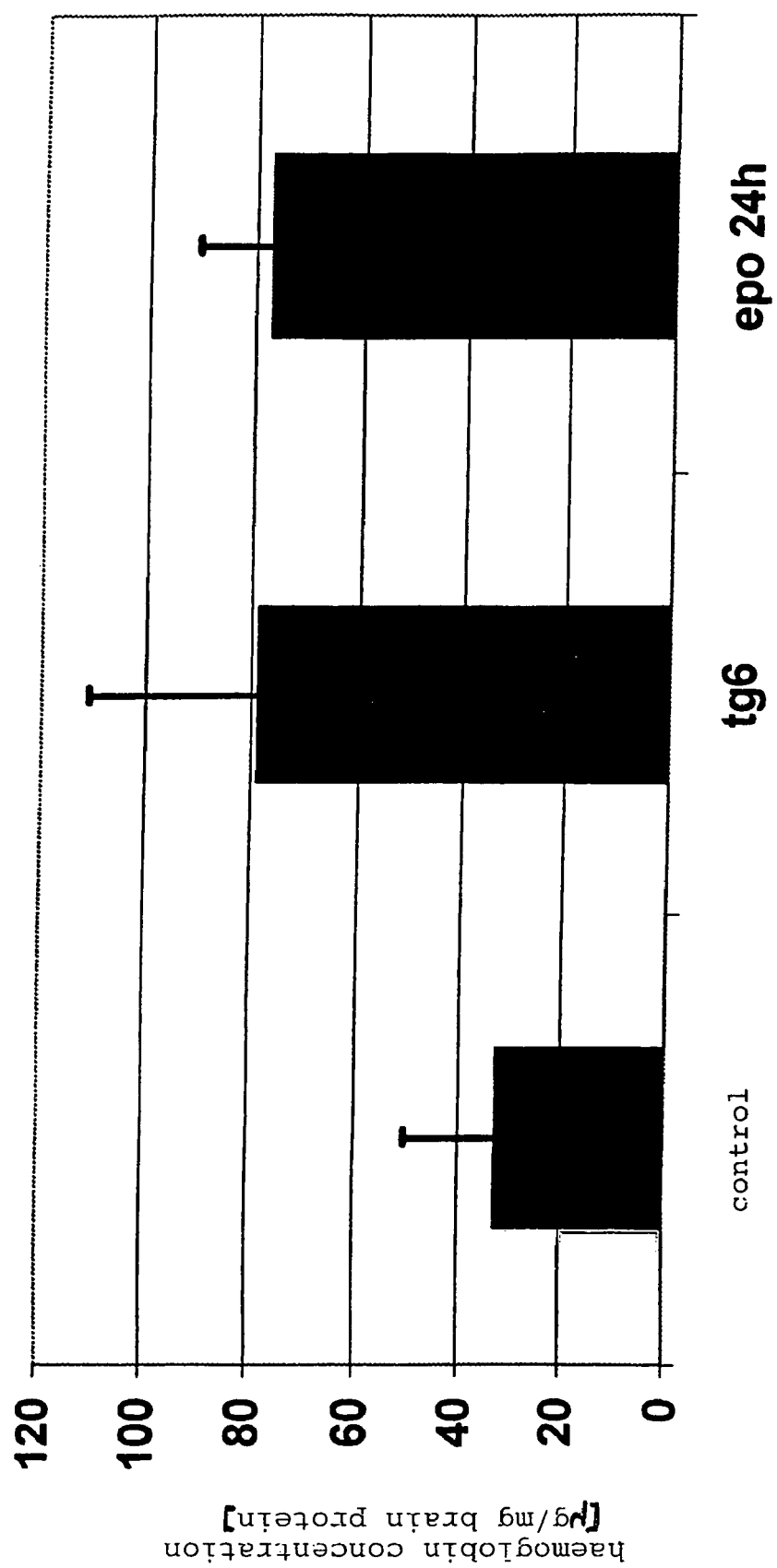
FIG. 14 shows, in the form of a bar chart, the results of a test to measure the protein of haemoglobin as a proportion of the overall protein in brain samples after intraperitoneal erythropoetin injection.

In continuation of Example 3, the haemoglobin concentration was also determined in the brain of mice to whom intraperitoneal erythropoetin (Erypo made by the company Janssen) had been administered (5000 units/kg body weight). After injection of EPO, the mice were terminally anaesthetised after 24 hours by injection with Rompun/Ketanest, and the blood was rinsed out of the vascular system of the brain by transcardial perfusion with 40 ml Hanks balanced salt solution (HBSS). For this, a brain homogenate was produced in 2 ml sample buffer consisting of 40 minol/l tris, 7 mol/l urea, 2 mol/l thiourea, 4% (w/v) CHAPS, 10 minol/l DTT and 1 minol/l EDTA homogenised and centrifuged for 45 min at 100,000×g. The protein content of the samples was determined according to the Bradford method (Bradford, 1976, Anal. Biochem. 72, 248-254). The haemoglobin concentration was measured with the rapid cyanhaemiglobin method (van Kampen and Zijlstra, 1961, Clin. Chim. Acta 6, 538-544). Then 20 μl of the corresponding brain homogenate samples were added to 5 ml of a transformation solution consisting of 200 mg/l potassium hexacyanoferrate, 50 mg/l potassium cyanide, 140 mg/l potassium dihydrogen phosphate and 0.05% (v/v) Triton X-100 and incubated for at least 5 min at room temperature. The extinction at 546 nm was then measured and multiplied by 36.7 to obtain the concentration in g/dl. These values were then related to the protein concentration/volume brain tissue, giving the following values (including the measured transgenic animals from Example 3): control animals: 32.54±17.51 μg/mg brain protein (n=10); EPO-transgenic animals (line tg6): 79.00±32.12 (n=13); EPO-injected animals (24 hours after injection): 77.14±13.51 μg/mg brain protein (n=3). The difference between the control and EPO-treated animals or EPO-transgenic animals was significant (ANOVA and post-hoc test) (FIG. 14). These data show that a single EPO injection for which a neuroprotective effect has been shown leads to a measurable increase in the concentration of intact haemoglobin in the brain. This underlines the functional relevance of globin induction by EPO in the central nervous system.

Example 9

Induction of Key Enzymes in Haem Synthesis by Erythropoetin in the Brain

We were able to prove in Examples 3, 5 and 8 that intact haemoglobin is formed in the brain by neurones and is induced by erythropoetin. Examples 2, 4 and 6 prove that EPO directly increases the quantity of messenger RNA for alpha and beta globin. Haemoglobin contains, however, in addition to the protein portions α and β globin (in adults), the prosthetic group haem. Haem is present in neurones and can be broken down by haemoxygenase. The synthesis of haem is known precisely. Synthesis starts with the condensation of glycine and succinyl CoA to δ-aminolaevulinic acid. The enzyme that catalyses this step is δ-aminolaevulinic acid synthase (ALAS). This synthesis is usually the important rate-limiting step in haem synthesis. In the next step, the porphobilinogen synthase, which is also called aminolaevulinic acid dehydratase (abbreviated to DALDH) catalyses the condensation of two molecules δ-aminolaevulinic acid to porphobilinogen (PBG).

Surprisingly, we found that the mRNA for DALDH showed an induction (data not shown) on the DNA array (see Example 1). We then verified the high regulation for DALDH and ALAS using the quantitative PCR in the LightCycler (Roche). The primer sequences used and PCR conditions were, for ALAS:

```
alas_m_LC.sub.--ls:              (SEQ ID NO:10)
ACAGACCTGCTGAGCACCATG alas_m_LC_las:                   (SEQ ID NO:11)
AGCCAGCTCCTGTTCAAGCTC
```

(annealing temperature: 60 C.; measurement temperature: 83 C.; 45 cycles), and for DALDH: Daldh_m.sub.—1 s: ccaactattgaggctgtccgt (SEQ ID NO:12), daldh_m.sub.—1 as: catgagcatgtcagctccttc (SEQ ID NO: 13) (annealing temperature: 60 C.; measurement temperature: 85 C.; 45 cycles).

Figure 15:
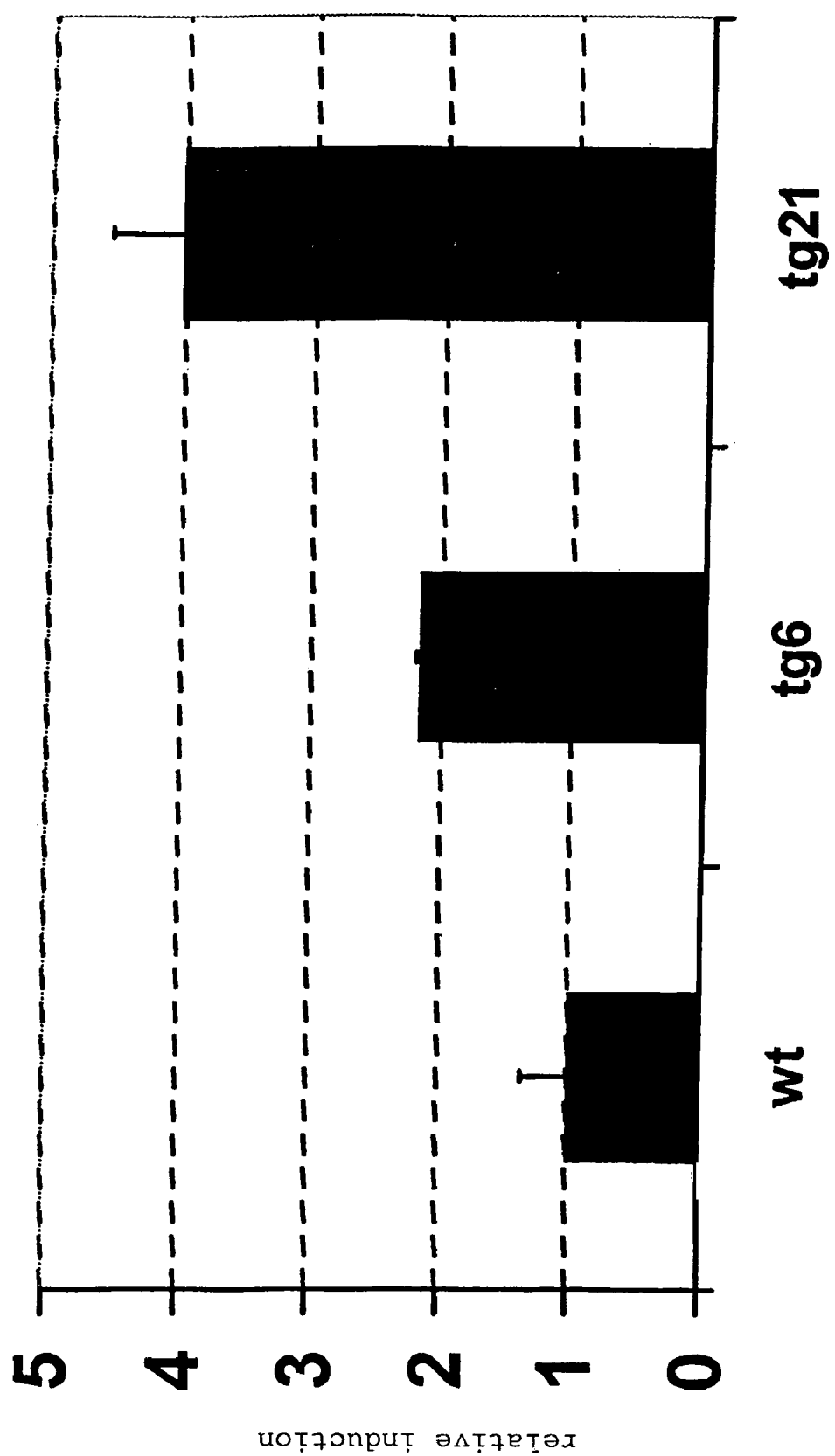
FIG. 15 shows the result of a quantitative PCR for DALDH in wild type (wt) and EPO-transgenic animals.
Figure 16:
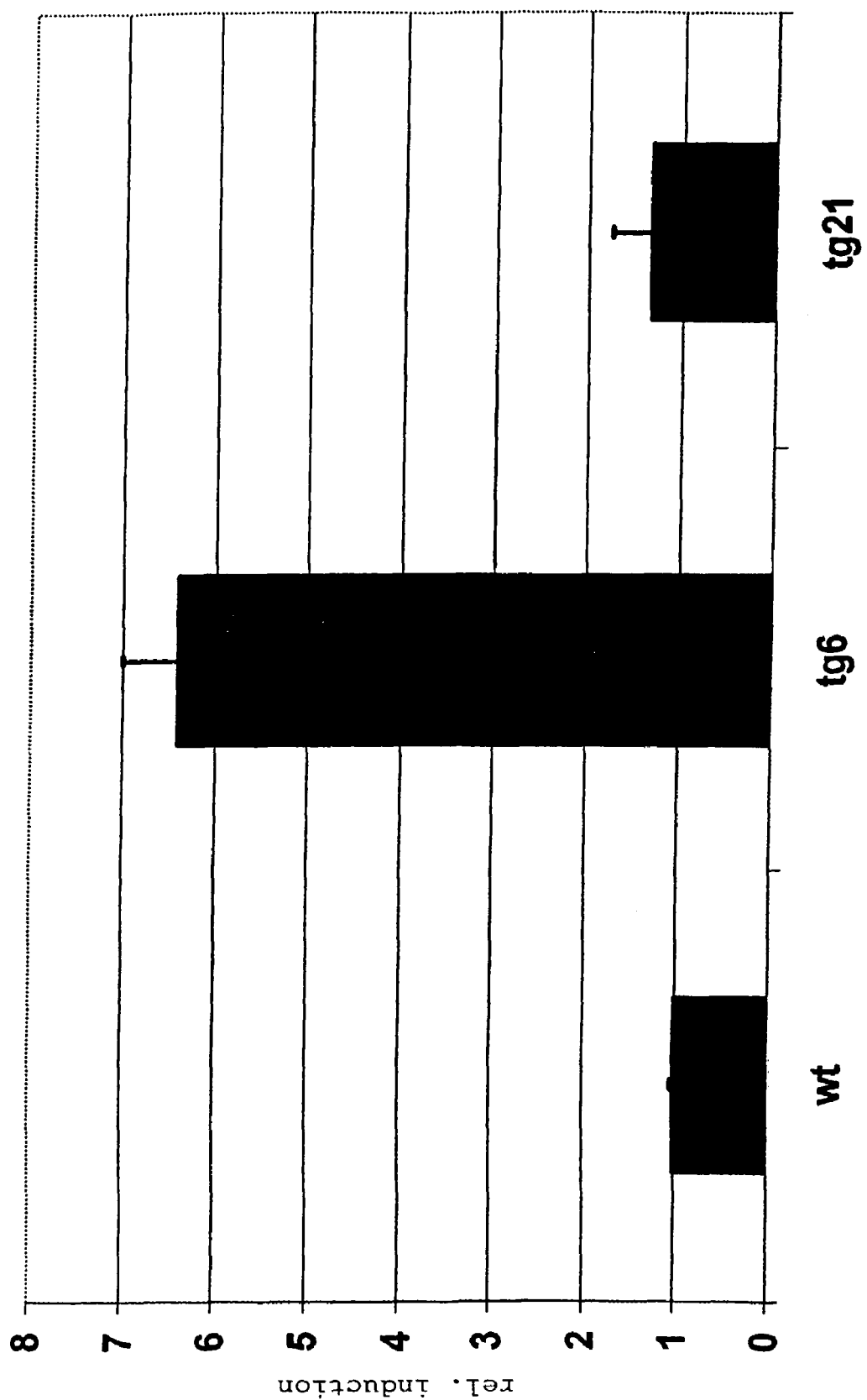
FIG. 16 shows the result of a quantitative PCR for ALAS in wild type (wt) and EPO-transgenic animals.
Figure 17:
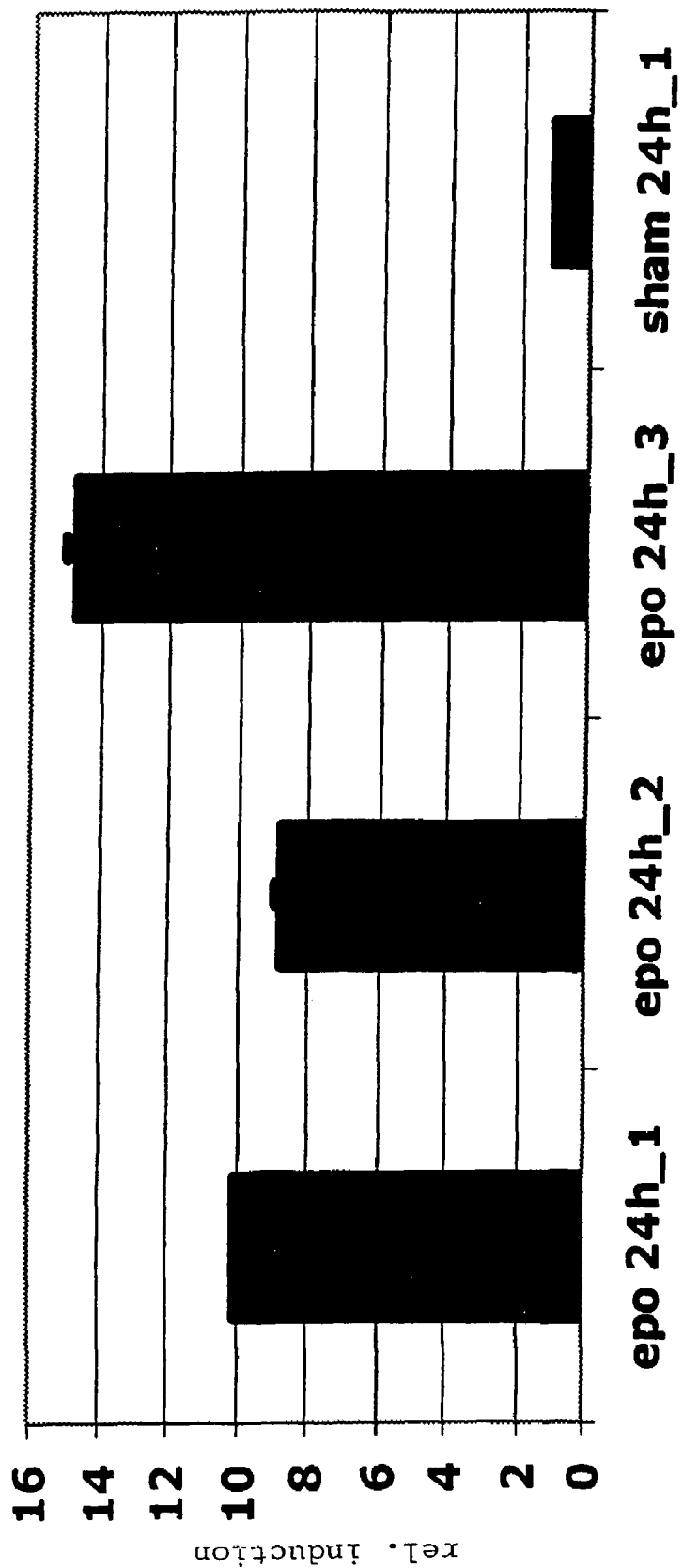
FIG. 17 shows the result of a quantitative PCR for ALAS in EPO-injected animals after 24 hours.
Figure 18:
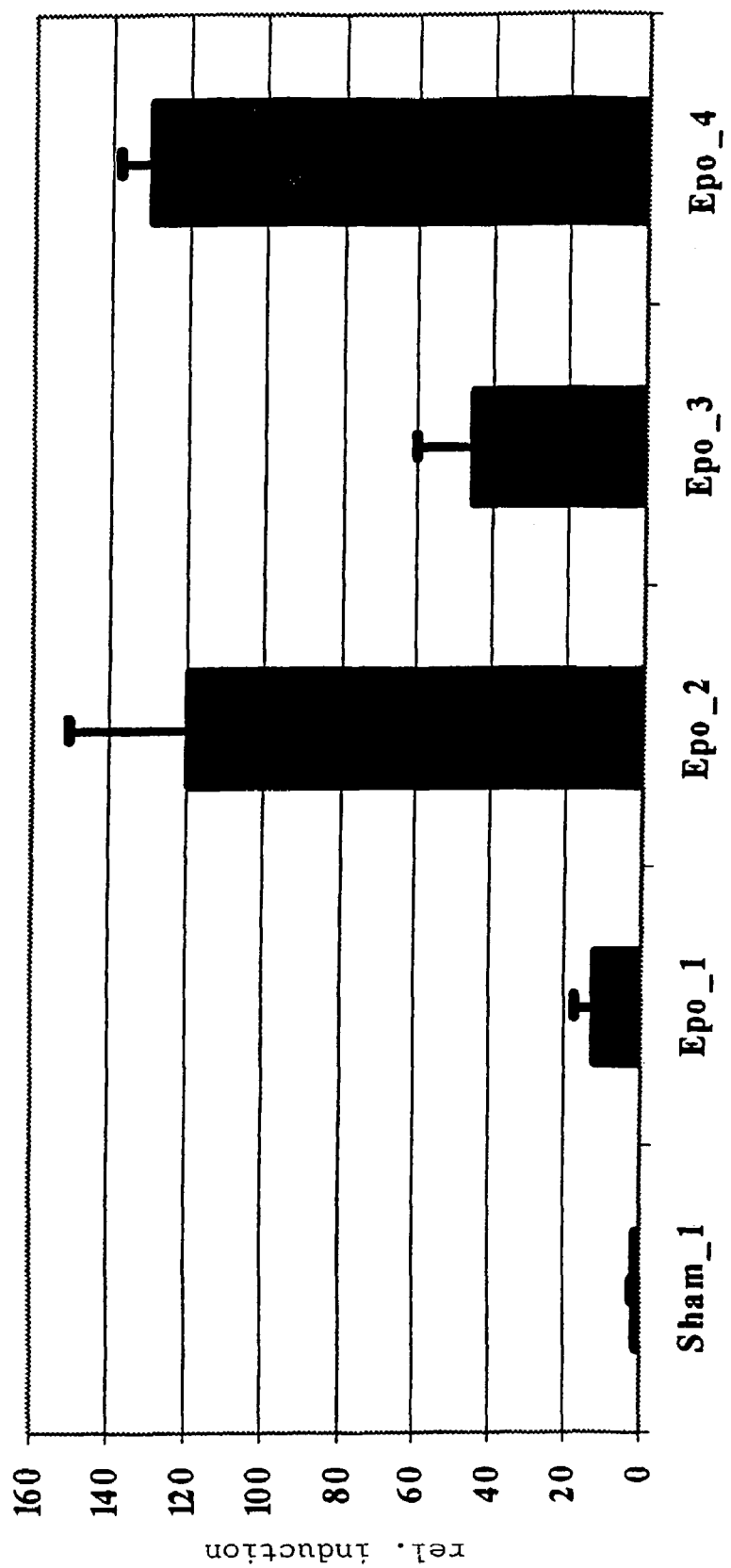
FIG. 18 shows the result of a quantitative PCR for ALAS in EPO-injected animals after 7 days.

DALDH showed, in the EPO overexpressing animals of lines tg6 and tg21, an increased expression: wild type (wt) 1±0.35, tg6 2.18±0.02, tg21 4.02±0.55 (FIG. 15). ALAS also showed, in the EPO overexpressing animals of lines tg6 and tg21, an increased expression: wild type (wt) 1±0.04, tg6 6.39±0.60, tg21 1.33±0.42 (FIG. 16). In addition, we were able to prove for ALAS that it can also be induced at mRNA level directly by injection of a one-off dose of EPO (5000 units/kg body weight i.p.): sham (sham 24 h_2): 1.00±0.08; EPO-injected animal 1 (epo 24 h_1): 10.07±0.00; EPO-injected animal 2 (epo 24 h_2): 8.76±0.18; EPO-injected animal 3 (epo 24 h_3): 14.69±0.27 (FIG. 17). Through the daily administration of this dosage of EPO for 7 days, induction factors of up to 130 times were achieved: sham: 1±0.64; EPO-injected animal 1 (Epo_1)=11.67±5.46; EPO-injected animal 2 (Epo_2)=118.93±31.02; EPO-injected animal 3 (Epo_3)=44.88±15.15; EPO-injected animal 4 (Epo_4)=129.47±8.77 (FIG. 18).

Example 10

Neuroglobin is not Induced by a Single Erythropoetin Injection

Figure 19:
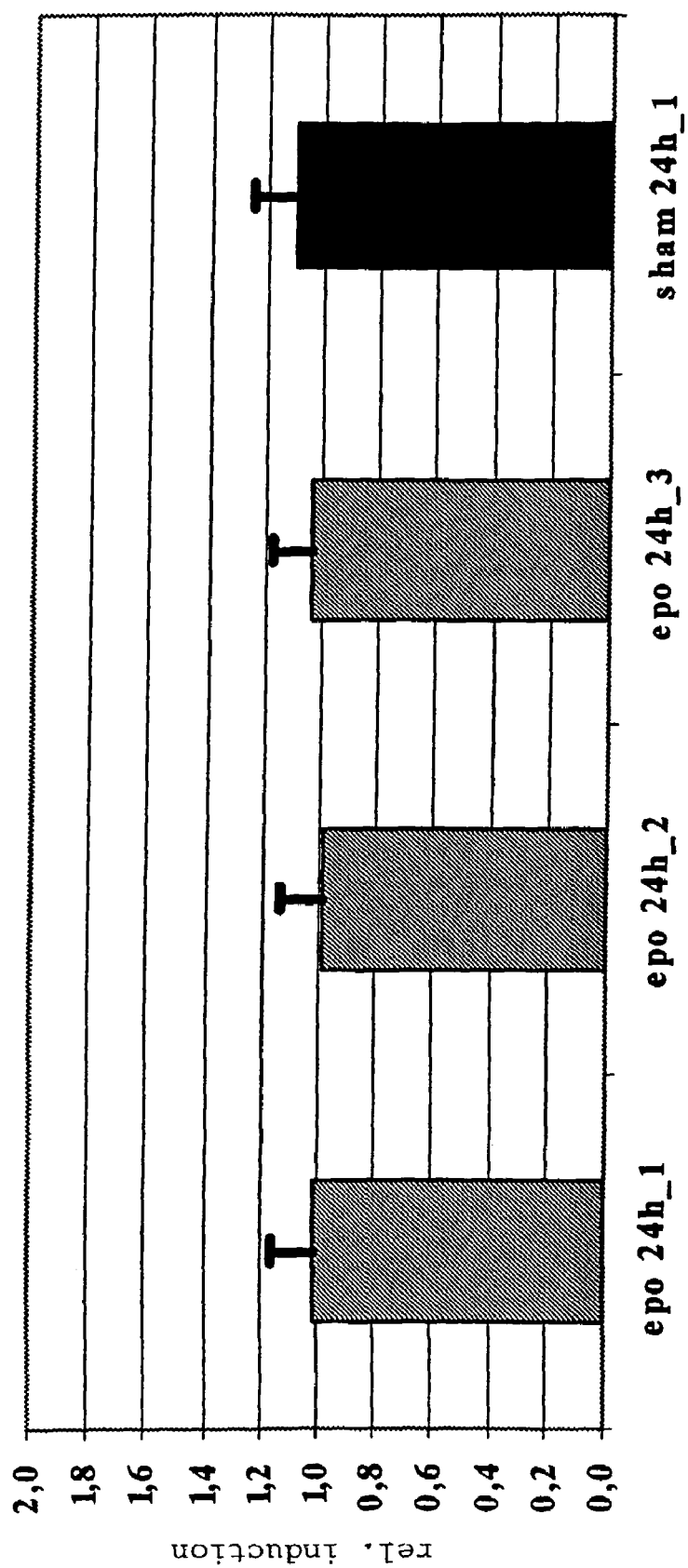
FIG. 19 shows the result of a quantitative PCR for neuroglobin after erythropoetin injection.

Neuroglobin is a protein that shows a minor homology to globins and which is also found in the central nervous system (Trent et al. (2001), Journal of Biological Chemistry, 276, 30106-10). However, it has important biochemical characteristics which fundamentally distinguish it from the globins, e.g. a far higher oxygen affinity (Dewilde et al. (2001), Journal of Biological Chemistry, 276, 38949-55). Neuroglobin is neuroprotective, although the mechanism here is not known (Sun et al. (2001), Proc. Natl. Acad. Sci. USA, 98, 15306-11, Venis (2001), Lancet, 358, 2055, Sun et al. (2003), Proc. Natl. Acad. Sci. USA, 5, 5). To determine whether neuroglobin possibly also plays a role in erythropoetin-conveyed neuroprotection, the relative content of neuroglobin mRNA after EPO administration was determined using relative quantitative PCR in comparison with cyclophilin. 5000 units of EPO/ kg body weight were applied i.p. and the animals were killed after transcardial perfusion. RNA and cDNA were obtained using standard methods. From serial dilutions of the cDNA (3 times serial dilutions), the levels of cyclophilin and neuroglobin were determined and the ratio of neuroglobin/cyclophilin in the sham-treated animals set at 1. The standard deviations in the following values relate to measurements at different dilutions (n=4) and represent the measurement accuracy. The primers used were: ng1_m_LC.sub.—1s: gagtcagagctgatccg-gcag (SEQ ID NO: 14), ng1_m_LC.sub.—1as: caggcacttctc-cagcatgta (SEQ ID NO: 15) for neuroglobin. The primers for cyclophilin were: cyc5, ACC CCA CCG TGT TCT TCG AC (SEQ ID NO: 1); acyc300, CAT TTG CCA TGG ACA AGA TG (SEQ ID NO:2). The annealing temperature chosen was 60 C., the measurement temperature for PCR products was 86 C., and 45 cycles were carried out in all. It was found that no induction of neuroglobin occurred (sham: 1.10±0.15; EPO-injected animal 1: 1.01±0.15; EPO-injected animal 2: 0.99±0.15; EPO-injected animal 3: 1.04±0.13; FIG. 19) in the same animals in which .alpha. and .beta. globin and .delta.-aminolaevulinic acid synthase (ALAS) were strongly induced at this time (.alpha. globin approx. 14 times, .beta. globin approx. 10 times, ALAS approx. 10 times as much, see also examples above). It can be concluded from these data that neuroglobin is not involved in erythropoietin-conveyed neuroprotection which is mediated by the influence of gene expression.

Example 11

Functional Relevance of Intracellular Haemoglobin for Neuronal Cells (PC12 Cells)

Figure 20:
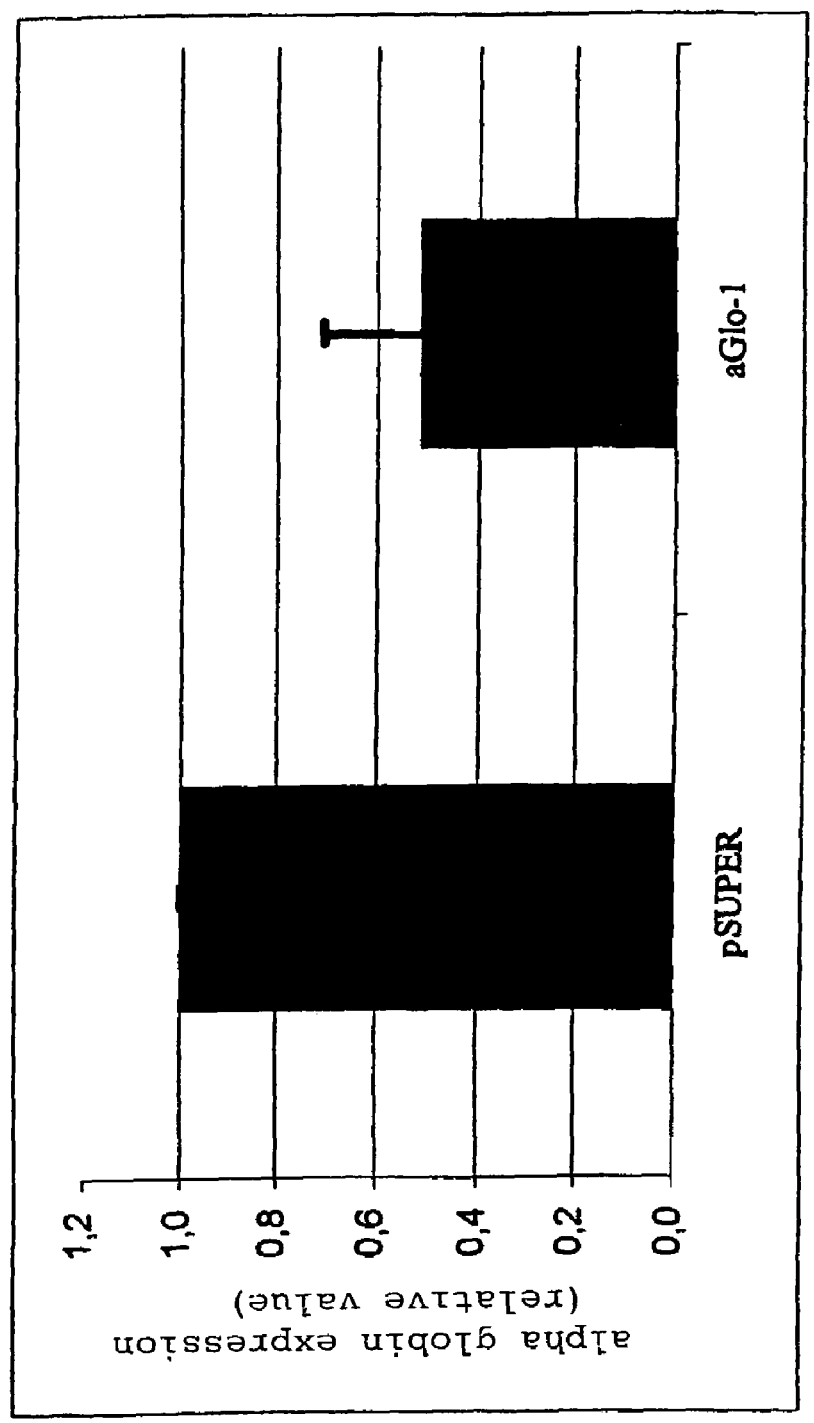
FIG. 20 shows the result of a quantitative PCR for alpha globin mRNA for determining the effectiveness of the siRNA construct pSaGlo1 in transiently transfected PC12 cells.

The publication by Bruminelkamp, et al. (2002): Science 19 (296): 550-3 describes a vector which makes it possible to express short, double-stranded antisense RNA molecules in cells, leading to the breakdown of the mRNA of the specific target gene (siRNA). This method should be applied to confirm the neuroprotective effect of neuronal globin. Firstly, the vector pSUPER was produced as described (Bruminelkamp et al., 2002). After this, alpha globin specific DNA oligos, designed according to Bruminelkamp et al., 2002, were synthesised (Thermohybaid/Thermo Biosciences GmbH; aGlo 1-s: 5'-p-GATCCCCTTCCTTGCCTCTG-TGAGCATTC-MGA GATGCTCACAGAGGCAAGGAATTTTTGGAAA-3' (SEQ ID NO: 16) and aGlo1-as: 5'-p-GCTTTTC-CAAAAA TTCCTTGCCTCTGTGAGCATCTCTTGMT-GCTCACAGAGGCAAGGMGGG-3'(SEQ ID NO: 17)) and hybridised with each other in a concentration of 10 μM in ligase buffer at gradually decreasing temperatures (95 C. to 40 C. over 15 min). This double-strand DNA oligomer was ligated in the BgIII-HindIII double-digested pSUPER. The construct created in this way was designated pSaGlo1. This construct and the empty vector pSUPER were transiently transfected in each case together with an expression construct for alpha globin and an expression construct for an independent gene in PC12 cells. Two days after the transfection, the cells were harvested and the total RNA was isolated from these cells. The effectiveness of the downward regulation of the alpha globin mRNA by the siRNA construct was examined by means of quantitative RT-PCR in a LightCycler (Roche Diagnostics, Mannheim, Germany). The measure for the transfection efficiency was the mRNA level of the independent gene, which was also measured by RT-PCR and used as a reference (primers used: Rm_a_glob.sub.—1s: 5'-GG-GAAGATTGGTGGCCATGGTG-3' (SEQ ID NO:6); Rm_a_ glob.sub.—1as: 5'-GGCAAGGATTTGTCCA-GAGAGGC-3' (SEQ ID NO:7); annealing temperature 60 C.; measurement temperature: 85 C.; 50 cycles). In independent experiments, it was shown that in spite of an overexpression of the target gene, the RNA quantity was reduced to around half (FIG. 20). For this, the measured alpha globin values in the pSUPER transfected cells were set at 1 (pSUPER=1±0) and those of the pSAGo1 were seen in relation to this (aGlo1=0.5±0.2).

Figure 21:
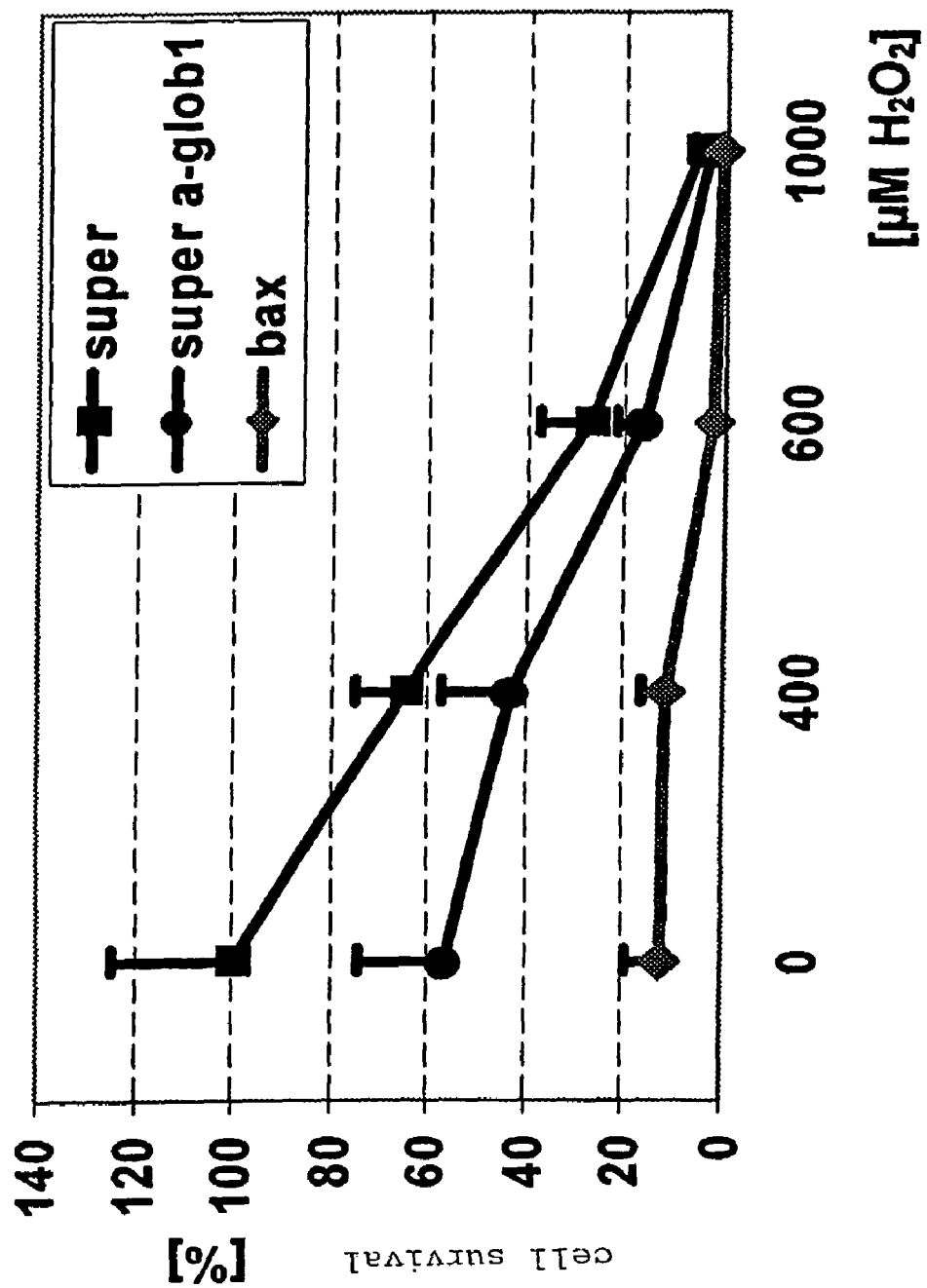
FIG. 21 shows the results of a measurement to determine the effect of alpha globin mRNA on the ability of cells to survive. Cell survival in % was measured after the transfection of PC12 cells with the siRNA construct pSaGlo1.

In further tests, the effect of alpha globin on the ability of cells to survive was tested. PC12 cells were sown in poly-L-lysin coated LIA 96-well plates with a flat base. After 2 days in culture, the cells were transfected with *Renilla luciferase* expression constructs and pSUPER or pSaGlo1 or a bax expression construct. After a further day in the culture, the cells were exposed to $H_2O_2$ in various concentrations. 20 h after the $H_2O_2$ stimulus, the survival of the transfected cells was determined using a luciferase assay (according to the manufacturer's instructions: Promega: *Renilla Luciferase Assay System*; Berthold: Mithras Platereader). A higher luciferase activity indicates a larger number of living transfected cells. Cells in which the alpha globin mRNA expression was lowered by the siRNA construct pSaGlo1 (pSUPER aGlob1) react with cell death more sensitively to $H_2O_2$ than cells transfected with the empty vector pSUPER (FIG. 21). This indicates a possible neuroprotective function of intracellular haemoglobin in neuronal cells.

The invention claimed is:

1. A screening method for the identification of a neuroprotective substance which increases haemoglobin formation in neuronal cells, comprising:
    bringing the substance to be tested into contact with a neuronal test cell, and
    detecting an increased haemoglobin formation in the neuronal test cell,
    wherein the neuronal test cell is (a) a cultured cell or (b) a cell of an animal wherein blood is removed from the test cell before the detecting step.

2. The method according to claim 1, wherein the detection of the increased haemoglobin formation is carried out by the detection of at least one globin RNA.

3. The method according to claim 2, wherein the globin RNA to be detected is alpha globin and/or beta globin RNA.

4. The method according to claim 2, wherein the detection of globin RNA is carried out by a polymerase chain reaction (PCR).

5. The method according to claim 2, wherein the detection of globin RNA is carried out by hybridisation with a suitable probe.

6. The method according to claim 1, wherein the detection of the increased haemoglobin formation is carried out by the detection of haemoglobin protein.

7. The method according to claim 6, wherein the detection of haemoglobin protein is carried out by staining with 2,7-diaminfluorene or with the cyanhaemiglobin method.

8. The method according to claim 6, wherein the detection of haemoglobin protein is carried out with an antibody.

9. The method according to claim 1, wherein the neuroprotective substance is not erythropoietin.

10. A screening method for the identification of a neuroprotective substance which increases haemoglobin formation in neuronal cells, comprising:
    bringing one or more neuronal test cells into contact with a plurality of substances from a chemical library, and
    detecting an increased haemoglobin formation in a neuronal test cell.

* * * * *

UNITED STATES PATENT AND TRADEMARK OFFICE
CERTIFICATE OF CORRECTION

PATENT NO. : 7,575,857 B2  Page 1 of 1
APPLICATION NO. : 10/507710
DATED : August 18, 2009
INVENTOR(S) : Maurer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 343 days.

Signed and Sealed this

Seventh Day of September, 2010

David J. Kappos
*Director of the United States Patent and Trademark Office*